United States Patent [19]

Gelvin

[11] Patent Number: 4,771,002
[45] Date of Patent: Sep. 13, 1988

[54] TRANSCRIPTION IN PLANTS AND BACTERIA

[75] Inventor: Stanton B. Gelvin, West Lafayette, Ind.

[73] Assignee: Lubrizol Genetics, Inc., Wickliffe, Ohio

[21] Appl. No.: 584,244

[22] Filed: Feb. 24, 1984

[51] Int. Cl.$^4$ .................. C12N 15/00; C12N 1/20
[52] U.S. Cl. .................. 435/172.3; 435/253; 435/320; 935/30; 935/35; 935/56; 935/72
[58] Field of Search .................. 435/172.3, 68, 317, 435/253, 320; 935/30, 35, 56, 67; 200/1

[56] References Cited

FOREIGN PATENT DOCUMENTS 0145338 6/1985 European Pat. Off. .

OTHER PUBLICATIONS

Goodman et al., 1987, Science 236: 48–54.
Gelvin et al., 1981, Plasmid, v 6, pp. 17–29.
Karcher et al., 1984, Mol. Gen. Genet, v 194, pp. 159–165.
Herrera-Estrella et al., 1983, EMBOJ, v 2, pp. 987–995.
Thomashow et al., 1980, "Integration and Organization of Ti Plasmid Sequences in Crown Gall Tumors", Cell, v 19, 729–39.
Bevan, M. W. et al., (1983), Nature, v 304, pp. 184–187.
Fraley et al., (1983), Proc Natl Acad Sci, v 80, pp. 4803–4807.
Herrera-Estrella et al., (1983), Nature, v 303, pp. 209–213.
Murai et al., (1982), Nucleic Acids Res, v 10, pp. 1679–1689.
Caplan et al., 1984, pp. 480–493, In: Biotechnology and Biological Frontiers, AAAS, Washington, D.C.
Schröder et al., (1983), EMBO J., 2(3):403–409.
Sciaky et al., (1978), Plasmid 1:238–253.
Jorgensen et al., (1979), Molec. Gen. Genet., 177:65–72.
Pouwels et al., (1985), Cloning Vectors: A Laboratory Manual (Elsevier, Amsterdam, Netherlands), pp. I-A-IV-20, II-A-a-i-1 and reference pages.
Barker et al., (1983), Plant Mol. Biol., 2:335–350.
Hooykaas-van Slogteren et al., (1984), Nature, 311:763–764.
Hernalsteens et al., (1984), EMBO J., 3:3039–3041.

Primary Examiner—Charles F. Warren
Assistant Examiner—David T. Fox
Attorney, Agent, or Firm—Greenlee and Associates

[57] ABSTRACT

A promoter region that drives expression of a 1450 base $T_R$ transcript in octopine-type crown gall tumors can also promote expression of a foreign structural gene in bacteria. Use of this dul-purpose promoter region to drive expression of a single copy of a foreign structural gene in both plants and bacteria is taught. The construction of a selectable marker functional in eukaryotes and prokaryotes is exemplified, as are vectors useful in efforts to transform plants.

24 Claims, 3 Drawing Sheets

TRANSCRIPTION IN PLANTS AND BACTERIA

FIELD

The present invention is in the fields of genetic engineering and plant husbandry, and especially provides means for promotion of transcription in and selectable markers for both plants and bacteria.

BACKGROUND

Following are publications which disclose background information closely related to the present invention. These publications are discussed in greater depth in the Background sections indicated. M. W. Bevan et al. (1983) Nature 304:184–187, R. T. Fraley et al. (1983) Proc. Natl. Acad. Sci. USA 80:4803–4807, and L. Herrera-Estrella et al. (1983) Nature 303:209–213, disclosed use of the nos promoter to drive expression in plants of bacterial antibiotic resistance structural genes (see Manipulations of the TIP Plasmids). R. F. Barker et al. (1983) Plant Molec. Biol. 2:335–350, and R. F. Barker and J. D. Kemp, U.S. patent application Ser. No. 553,786 disclose the complete sequence of the T-DNA from the octopinetype plasmid pTi15955; homologous published sequences of other Ti plasmid genes are referenced therein (Genes on the TIP Plasmids). N. Murai and J. D. Kemp (1982) Nucleic Acids Res. 10:1679–1689, disclosed the existance and approximate location of a 1450 base transcript (1450bTx), identified therein as having a size of 1600 bases, encoding open reading frame (ORF) 24 of the sequence. S. B. Gelvin et al. (1981) Plasmid 6:17–29, disclosed that $T_R$ is transcribed in Agrobacterium cells and in plant cells (Genes on the TIP Plasmids). S. J. Karcher et al. (1984) Mol. Gen. Genet., mapped the position of the 1450bTx (Example 1). The dual-purpose functional properties derived from the 1450bTx promoter region (1450bTxPR), as disclosed and taught herein, were not reported in the aforementioned references. L. Herrera-Estrella et al. (1983) EMBO J. 2:987–995, reported that structural genes encoding resistances to kanamycin and methotrexate were expressed in both bacterial and plant cells when placed behind the nos promoter.

Shuttle Vectors

Shuttle vectors, developed by G. B. Ruvkun and F. M. Ausubel (1981) Nature 298:85–88, provide a way to insert foreign genetic materials into position of choice in a large plasmid, virus, or genome. There are two main problems encountered when dealing with large plasmids or genomes. Firstly, the large plasmids may have many sites for each restriction enzyme. Unique site-specific cleavage reactions are not reproducible and multi-site cleavage reactions followed by ligation lead to great difficulties due to the scrambling of the many fragments whose order and orientation one does not want changed. Secondly, the transformation efficiency with large DNA plasmids is very low. Shuttle vectors allow one to overcome these difficulties by facilitating the insertion, often in vitro, of the foreign genetic material into a smaller plasmid, followed by transfer, usually by in vivo techniques, to the larger plasmid.

A shuttle vector consists of a DNA molecule, usually a plasmid, capable of being introduced into the ultimate recipient bacteria having a replicon that can be maintained independently therein. It also includes a copy of the fragment of the recipient genome into which the foreign genetic material is to be inserted and a DNA segment coding for a selectable trait, which is also inserted into the recipient genome fragment. The selectable trait ("marker") is conveniently inserted by transposon mutagenesis in vivo or by in vitro use of restriction enzymes and ligases.

The shuttle vector can be introduced into the ultimate recipient cell, typically a bacterium of the family Rhizobiaceae (which contains the genus Agrobacterium), by a tri-parental mating (Ruvkin and Ausubel, supra), direct transfer of a self-mobilizable vector in a bi-parental mating, direct uptake of exogenous DNA by Agrobacterium cells ("transformation", using the conditions of M. Holsters et al. (1978) Molec. Gen. Genet. 163:181–187), by spheroplast fusion of Agrobacterium with another bacterial cell, by uptake of liposome-encapuslated DNA, or infection with a shuttle vector that is based on a virus that is capable of being packaged in vitro. A tri-parental mating, a technique well known to those skilled in the art of manipulation of large plasmids found in members of the family Rhizobiaceae, involves the mating of a strain containing a mobilizable plasmid, which carries genes for plasmid mobilization and conjugative transfer, with the strain containing the shuttle vector. If the shuttle vector is capable of being mobilized by the plasmid genes, the shuttle vector is transferred to the recipient cell containing the large genome, e.g. the Ti or Ri plasmids of Agrobacterium strains.

After the shuttle vector is introduced into the recipient cell, possible events include a double cross-over with one recombinational event on either side of the marker. This homogenotization event will result in transfer of a DNA segment containing the marker to the recipient genome replacing a homologous segment lacking the insert. To select for cells that have lost the original shuttle vector, the shuttle vector must be incapable of replicating in the ultimate host cell or be incompatible with an independently selectable plasmid pre-existing in the recipient cell. One common means of arranging this is to provide in the third parent another plasmid which is incompatible with the shuttle vector and which carries a different drug resistance marker. Therefore, when one selects for resistance to both drugs, the only surviving cells are those in which the marker on the shuttle vector has recombined with the recipient genome. If the shuttle vector carries an extra marker, one can then screen for and discard cells that contain plasmids resulting from a single cross-over event between the shuttle vector and the recipient plasmid resulting in cointegrates in which the entire shuttle vector is integrated with the recipient plasmid. If the foreign genetic material is inserted into or adjacent to the marker that is selected for, it will also be integrated into the recipient plasmid as a result of the same double recombination. It might also be carried along when inserted into the homologous fragment at a spot not within or adjacent to the marker, but the greater the distance separating the foreign genetic material from the marker, the more likely will be a recombinational event occurring between the foreign genetic material and marker, preventing transfer of the foreign genetic material.

If the shuttle vector is used to introduce a phenotypically dominant trait (e.g. a novel expressible insecticide structural gene, but not an inactivated oncogenic T-DNA gene) one need not rely on a double homologous recombination. The cells resulting from a single cross-over event resulting in cointegrate plasmids can transfer the desired trait into plant cells (A. Caplan et al. (1983) Science 222:815-821, R. B. Horsch et al. (1984) Science 223:496-498). One may even use a variant shuttle vector having a single uninterrupted sequence of T-DNA. However, as the resulting T-DNA will now contain a tandem duplication, one must be vigilant regarding a possible rare deletion of the shuttle vector by a single homologous recombination event occurring between the two homologous sequences in either the Agrobacterium or plant cells.

Shuttle vectors have proved useful in manipulation of Agrobacterium plasmids: see D. J. Garfinkel et al. (1981) Cell 27:143-153, A. J. M. Matzke and M.-D. Chilton (1981) J. Molec. Appl. Genet. 1:39-49, and J. Leemans et al. (1981) J. Molec. Appl. Genet. 1:149-164, who referred to shuttle vectors by the term "intermediate vectors" or "iV".

A recently disclosed variation of the shuttle vector system for inserting changes into large DNA molecules is the "suicide vector". In this system, as described by A. Puhler et al., U.S. application Ser. No. 510,370, which is hereby incorporated by reference, and R. Simon et al. (1983) Biotechnol. 1:784-791, the shuttle vector replicon cannot be maintained independently within the recipient cell. This property eliminates the need to introduce an incompatable plasmid into the recipient cell in order to exclude the shuttle vector as is commonly done during a triparental mating. All vector sequences which do not integrate into some already present DNA effectively "commit suicide" by not being replicated. As can be done with traditional types of shuttle vectors, one may distinguish between double and single homologous by screening for an antibiotic resistance gene which is not between the two regions of homology. Use of suicide vectors to transfer DNA sequences into a Ti plasmid has also been reported by E. Van Haute et al. (1983) EMBO J. 2:411-417, L. Comai et al. (1982) Plant. Molec. Biol. 1:291-300, L. Comai et al. (1983) Plasmid 10:21-30, P. Zambryski et al. (1983) EMBO J. 2:2143-2150, and A. Caplan et al., supra. C. H. Shaw et al. (1983) Gene 28:315-330, report use of a suicide vector to introduce a foreign DNA into a Ti plasmid without also introducing a selectable marker by means of selection of a single homologous recombinant followed by screening for a double homologous recombinant.

An alternative to the use of homologous recombination for introduction of novel DNA sequences into T-DNA involves bacterial transposons. As described in the section Agrobacterium-Genes on the TIP Plasmids, transposons can "jump" into the T-DNA of a TIP plasmid (e.g. see D. J. Garfinkel et al. (1981) Cell 27:143-153). Should the transposon be modified in vitro by the insertion of the novel sequence, that novel DNA can be transferred into the TIP plasmid's T-DNA by the transposon. The TIP can then transfer the novel DNA/transposon/T-DNA combination to a plant cell when it will be stably integrated.

Overview of Agrobacterium

Included within the gram-negative bacterial family Rhizobiaceae (which also includes the genus Rhizobium), in the genus Agrobacterium, are the species *A. tumefaciens* and *A. rhizogenes*. These species are respectively the causal agents of crown gall disease and hairy root disease of plants. Crown gall is characterized by the growth of a gall of dedifferentiated tissue. Hairy root is a teratoma characterized by inappropriate induction of roots in infected tissue. In both diseases, the inappropriately growing plant tisssue usually produces one or more amino acid derivatives, known as opines, not normally produced by the plant which are catabolized by the infecting bacteria. Known opines have been classified into three main families whose type members are octopine, nopaline, and agropine. The cells of inappropriately growing tissues can be grown in culture, and, under appropriate conditions, be regenerated into whole plants that retain certain transformed phenotypes.

Virulent strains of Agrobacterium harbor large plasmids known as Ti (tumor-inducing) plasmids in *A. tumefaciens* and Ri (root-inducing) plasmids in *A. rhizogenes*. Curing a strain of these plasmids results in a loss of pathogenicity. The Ti plasmid contains a region, referred to as T-DNA (transferred-DNA), which in tumors is found to be integrated into the genome of the host plant. The T-DNA encodes several transcripts. Mutational studies have shown that some of these are involved in induction of tumorous growth. Mutants in the genes for tml, tmr, and tms, respectively result in large tumors (in tobacco), a propensity to generate roots, and a tendency for shoot induction. The T-DNA also encodes the gene for at least one opine synthase, and the Ti plasmids are often classified by the opine which they caused to be synthesized. Each of the T-DNA genes is under control of a T-DNA promoter. The T-DNA promoters resemble eukaryotic promoters in structure, and they appear to function only in the transformed plant cell. The Ti plasmid also carries genes outside the T-DNA region. These genes are involved in functions which include opine catabolism, oncogenicity, agrocin sensitivity, replication, and autotransfer to bacterial cells. The Ri plasmid is organized in a fashion analogous to the Ti plasmid. The set of genes and DNA sequences responsible for transforming the plant cell are hereinafter collectively referred to as the transformation-inducing principle (TIP). The designation TIP therefore includes, but is not limited to, both Ti and Ri plasmids. The integrated segment of a TIP is termed herein "T-DNA" (transferred DNA), whether derived from a Ti plasmid or an Ri plasmid.

M.-D. Chilton (June 1983) Sci. Amer. 248(6):50-59, has recently provided an introductory article on the use of Ti plasmids as vectors. Recent general reviews of Agrobacterium-caused disease include those by D. J. Merlo (1982), Adv. Plant Pathol. 1:139-178, L. W. Ream and M. P. Gordon (1982), Science 218:854-859, and M. W. Bevan and M.-D. Chilton (1982), Ann. Rev. Genet. 16:357-384; G. Kahl and J. Schell (1982) *Molecular Biology of Plant Tumors*, K. A. Barton and M.-D. Chilton (1983) Meth. Enzymol. 101:527-539, and A. Caplan et al. (1983) Science 222:815-821.

Infection of Plant Tissues

Plant cells can be transformed by Agrobacterium in a number of methods known in the art which include but are not limited to co-cultivation of plant cells in culture with Agrobacterium, direct infection of a plant, fusion of plant protoplasts with Agrobacterium spheroplasts, direct transformation by uptake of free T-DNA by plant cell protoplasts, transformation of protoplasts having partly regenerated cell walls with intact bacteria, transformation of protoplasts by liposomes containing T-DNA, use of a virus to carry in the T-DNA, microinjection, and the like. Any method will suffice as long as the gene is stably transmitted through mitosis and meiosis.

The infection of plant tissue by Agrobacterium is a simple technique well known to those skilled in the art (for an example, see D. N. Butcher et al. (1980) in *Tissue Culture Methods for Plant Pathologists*, eds.: D. S. Ingram and J. P. Helgeson, pp. 203-208). Typically a plant is wounded by any of a number of ways, which include cutting with a razor, puncturing with a needle, or rubbing with abrasive. The wound is then inoculated with a solution containing tumor-inducing bacteria. An alternative to the infection of intact plants is the inoculation of pieces of tissues such as potato tuber disks (D. K. Anand and G. T. Heberlein (1977) Amer. J. Bot. 64:153-158) or inverted segments of tobacco stems (K. A. Barton, et al. (1983) Cell 32:1033-1043). After induction, the tumors can be placed in tissue culture on media lacking phytohormones. Hormone independent growth is typical of transformed plant tissue and is in great contrast to the usual conditions of growth of such tissue in culture (A. C. Braun (1956) Cancer Res. 16:53-56).

Agrobacterium is also capable of infecting isolated cells and cells grown in culture (L. Maton et al. (1979) Nature 277:129-131) and isolated tobacco mesophyll protoplasts. In the latter technique, after allowing time for partial regeneration of new cell walls, Agrobacterium cells were added to the culture for a time and then killed by the addition of antibiotics. Only those cells exposed to *A. tumefaciens* cells harboring the Ti plasmid were capable of forming calli when plated on media lacking hormone. Most calli were found to contain an enzymatic activity involved in opine anabolism. Other workers (R. B. Horsch and R. T. Fraley (Jan. 18, 1983) 15th Miami Winter Symposium) have reported transformations by co-cultivation, leading to a high rate (greater than 10%) of calli displaying hormone-independent growth, with 95% of those calli making opines. M. R. Davey et al. (1980) in Ingram and Helgeson, supra, pp. 209-219, describe the infection of older cells that had been regenerated from protoplasts.

Plant protoplasts can be transformed by the direct uptake of TIP plasmids. M. R. Davey et al. (1980) Plant Sci. Lett. 18:307-313, and M. R. Davey et al. (1980) in Ingram and Helgeson, supra, were able to transform Petunia protoplasts with the Ti plasmid in the presence of poly-L-α-ornithine to a phenotype of opine synthesis and hormone-independent growth in culture. It was later shown (J. Draper et al. (1982) Plant and Cell Physiol. 23:451-458, M. R. Davey et al. (1982) in *Plant Tissue Culture* 1982, ed: A. Fujiwara, pp. 515-516) that polyethelene glycolstimulated Ti plasmid uptake and that some T-DNA sequences were integrated into the genome. F. A. Krens et al. (1982) Nature 296:72-74, reported similar results using polyethelene glycol following by a calcium shock, though their data suggests that the integrated T-DNA included flanking Ti plasmid sequences.

An alternative method to obtain DNA uptake involves the use of liposomes. The preparation of DNA-containing liposomes is well known in the art. Preparations for the introduction of Ti-DNA via liposomes have been reported (T. Nagata et al. (1982) in Fujiwara, supra, pp. 509-510, and T. Nagata (1981) Mol. Gen. Genet. 184:161-165). An analogous system involves the fusion of plant and bacterial cells after removal of their cell walls. An example of this technique is the transformation of Vinca protoplast by Agrobacterium spheroplasts reported by S. Hasezawa et al. (1981) Mol. Gen. Genet. 182:206-210. Plant protoplasts can take up cell wall delimited Agrobacterium cells (S. Hasezawa et al. (1982) in Fujiwara, supra pp. 517-518).

T-DNA can be transmitted to tissue regenerated from a fusion of two protoplasts, only one of which had been transformed (G. J. Wullems et al. (1980) Theor. Appl. Genet. 56:203-208). As detailed in the section on Regeneration of Plants, T-DNA can pass through meiosis and be transmitted to progeny as a simple Mendelian trait.

Regeneration of Plants

Differentiated plant tissues with normal morphology have been obtained from crown gall tumors. A. C. Braun and H. N. Wood (1976) Proc. Natl. Acad. Sci. USA 73:496-500, grafted tobacco teratomas onto normal plants and were able to obtain normally appearing shoots which could flower. The shoots retained the ability to make opines and to grow independently of phytohormones when placed in culture. In the plants screened, these tumorous phenotypes were not observed to be transmitted to progeny, apparently being lost during meiosis (R. Turgeon et al. (1976) Proc. Natl. Acad. Sci. USA 73:3562-3564). Plants which had spontaneously lost tumorous properties, or which were derived from teratoma seed, were initially shown to have lost all their T-DNA (F.-M. Yang et al. (1980) In Vitro 16:87-92, F. Yang et al. (1980) Molec. Gen. Genet. 177:707-714, M. Lemmers et al. (1980) J. Mol. Biol. 144:353-376). However, later work with plants that had become revertants after hormone treatment (1 mg/l kinetin) showed that plants which had gone through meiosis, though loosing T-DNA genes responsible for the transformed phenotype, could retain sequences homologous to both ends of T-DNA (F. Yang and R. B. Simpson (1981) Proc. Natl. Acad. Sci. USA 78:4151-4155). G. J. Wullems et al. (1981) Cell 24:719-724, further demonstrated that genes involved in opine anabolism were capable of passing through meiosis though the plants were male sterile and that seemingly unaltered T-DNA could be inherited in a Mendelian fashion (G. Wullems et al. (1982) in Fujiwara, supra). L. Otten et al. (1981) Molec Gen. Genet. 183:209-213, used Tn7 transposon-generated Ti plasmid mutants in the tms (shoot-inducing) locus to create tumors which proliferated shoots. When these shoots were regenerated into plants, they were found to form self-fertile flowers. The resultant seeds germinated into plants which contained T-DNA and made opines. In further experiments, H. DeGreve et al. (1982) Nature 300:752-755, have found that octopine synthase can be inherited as a single dominant Mendelian gene. However, the T-DNA had sustained extensive deletions of functions other than ocs while undergoing regeneration from callus. Similar experiments with a tmr (root-inducing) mutant showed that full-length T-DNA could be transmitted through meiosis to progeny, that in those progeny nopaline genes could be expressed, though at variable levels, and that cotransformed yeast alcohol dehydrogenase I gene was not expressed (K. A. Barton et al. (1983) Cell 32:1033-1043). Other experiments have shown that nopaline T-DNA is maintained during regeneration and that male sterile flowers pass on the T-DNA in a Mendelian fashion (J. Memelink et al. (1983) Mol. Gen. Genet. 190:516-522). Functional foreign genes are also inherited in a dominant Mendelian manner (R. B. Horsch et al. (1984) Science 223:496-498). It now appears that regenerated tissues which lack T-DNA sequences are decended from untransformed cells which "contaminate" the tumor (G. Ooms et al. (1982) Cell 30:589-597), and that the epigenetic state of the plant cells initially transformed can affect regeneration potential (G. M. S. vanSlogteren et al. (1983) Plant Mol. Biol. 2:321-333). Recent work by A. N. Binns (1983) Planta 158:272-279, indicates that tumorogenic genes, in this case tmr, can be "shut off" during regeneration and "turned back on" by placing regenerated tissue in culture.

Roots resulting from transformation from *A. rhizogenes* have proven relatively easy to regenerate directly into plantlets (M.-D. Chilton et al. (1982) Nature 295:432-434), and are easily cloned. Regenerability appears to be dependent on T-DNA copy-number (C. David et al. (1984) Biotechnol. -2:73-76).

Genes on the TIP Plasmids

The complete sequence of the T-DNA of an octopine-type plasmid found in ATCC 15955, pTi15955, has been reported and includes fourteen open reading frames (ORFs) flanked by eukaryotic transcriptional control sequences (R. F. Barker and J. D. Kemp, U.S. patent aplication Ser. No. 553,786, which is hereby incorporated by reference, R. F. Barker et al. (1983) Plant Molec. Biol. 2:335-350).

A number of genes have been identified within the T-DNA of the TIP plasmids. A number of octopine plasmid T-DNA transcripts have been mapped (S. B. Gelvin et al. (1982) Proc. Natl. Acad. Sci. USA 79:76-80, L. Willmitzer et al. (1982) EMBO J. 1:139-146, N. Murai and J. D. Kemp (1982) Nucleic Acids Res. 10:1679-1689, S. J. Karcher et al. (1984) Mol. Gen. Genet.) and some functions have been assigned (J. Leemans et al. (1982) EMBO J. 1:147-152). Some of these regions, specifically those encoding tmr and tms, can also be transcribed in prokaryotic cells (G. Schroder et al. (1983) EMBO J. 2:403-409). Genes of an octopine-type plasmid that have been well defined by transposon mutagenesis include tms, tmr, tml, and ocs (D. J. Garfinkel et al. (1981) Cell 27:143-153). Ti plasmids which carry mutations in these genes respectively incite tumorous calli of *Nicotiana tabacum* which generate shoots, proliferate roots, and are larger than normal. In other hosts, mutants of these genes can induce different phenotypes (see M. W. Bevan and M.-D. Chilton (1982) Ann. Rev. Genet. 16:357-384). The phenotypes of tms and tmr are correlated with differences in the phytohormone levels present in the tumor. The differences in cytokinin:auxin ratios are similar to those which in culture induce shoot or root formation in untransformed callus tissue (D. E. Akiyoshi et al. (1983) Proc. Natl. Acad. Sci. USA 80:407-411, A. N. Binns (1983) Planta 158:272-279, A. Caplan et al. (1983) Science 222:815-821, R. M. Amasino and C. O. Miller (1982) Plant Physiol. 69:389-392). T-DNA containing a functional gene for either tms or tmr alone, but not functional tml alone, can promote significant tumor growth. Promotion of shoots and roots is respectively stimulated and inhibited by functional tml (L. W. Ream et al. (1983) Proc. Natl. Acad. Sci. USA 80:1660-1664). Mutations in T-DNA genes do not seem to affect the insertion of T-DNA into the plant genome (Leemans et al. (1982) supra, Ream et al. (1983) supra). T-DNA genes need not be located between border sequences (see TIP Plasmid DNA) to promote hormone independent growth (H. Joos et al. (1983) EMBO J. 2:2151-2160).

Octopine Ti plasmids carry an ocs gene which encodes octopine synthase (lysopine dehydrogenase). The ocs gene does not contain introns (intervening sequences commonly found in eukaryotic genes which are posttranscriptionally spliced out of the messenger precursor during maturation of the mRNA). It does have sequences that resemble a eukaryotic transcriptional signal ("TATA box") and a polyadenylation site. All of the signals necessary for expression of the ocs gene are found within 295 bp of the ocs transcriptional start site (C. Koncz et al. (1983) EMBO J. 2:1597-1603). P. Dhaese et al. (1983) EMBO J. 2:419-426, reported the utilization of various polyadenylation sites by "transcript 7"(ORF3 of Barker et al., supra) and ocs. The presence of the enzyme octopine synthase within a tissue can protect that tissue from the toxic effect of various amino acid analogs (G. A. Dahl and J. Tempe (1983) Theor. Appl. Genet. 66:233-239, G. A. Dahl et al., U.S. patent application Ser. No. 532,280, which is hereby incorporated by reference).

Nopaline Ti plasmids encode the nopaline synthase gene (nos), which has been sequenced by A. Depicker et al. (1982) J. Mol. Appl. Genet. 1:561-573. As was found with the ocs gene, nos is not interrupted by introns. It has two polyadenylation sites and a potential "TATA box" transcriptional initiation signal. In contrast to ocs, nos is preceeded by a sequence which may be a transcriptional initiation signal known as a "CAT box". All of the signals necessary for expression of the nos gene are found within 261 bp of the nos transcriptional start site (C. Koncz et al., supra). A gene for agrocinopine synthase and genes equivalent to tms and tmr have been identified on a nopaline-type plasmid (H. Joos et al. (1983) Cell 32:1057-1067), and a number of transcripts have been mapped (L. Willmitzer et al. (1983) Cell 32:1045-1056). J. C. McPhersson et al. (1980) Proc. Natl. Acad. Sci. USA 77:2666-2670, reported the in vitro translation of T-DNA encoded mRNAs from crown gall tissues.

Transcription from hairy root T-DNA has also been detected (L. Willmitzer et al. (1982) Mol. Gen. Genet. 186:16-22). Functionally, the hairy root syndrome appears to be equivalent of a crown gall tumor incited by a Ti plasmid mutated in tmr (F. F. White and E. W. Nester (1980) J. Bacteriol. 144:710-720) as Ti plasmids mutated in tms and Ri plasmids can complement each other (G. M. S. van Slogteren (1983) Ph.D. thesis, Rijksuniversiteit te Leiden, Netherlands).

In eukaryotes, methylation (especially of cytosine residues) of DNA is correlated with transcriptional inactivation; genes that are relatively under methylated are transcribed into mRNA. S. B. Gelvin et al. (1983) Nucleic Acids Res. 11:159-174, has found that the T-DNA in crown gall tumors is always present in at least one unmethylated copy. That the same genome may contain numerous other copies of T-DNA which are methylated suggests that the copies of T-DNA in excess of one may be biologically inert. (See also G. Ooms et al. (1982) Cell 30:589-597.) Treatment of a tumor line with 5-azacytidine results in demethylation of a T-DNA gene which is parelleled by an increase in transcription (A. G. Hepburn et al. (1983) J. Mol. Appl. Genet. 2:315-329). 5-azacytidine treatment or grafting have been shown to activate silent opine genes (G. M. S. van Slogteren (1983) Ph.D. thesis, Rijksuniversiteit te Leiden, Netherlands).

The Ti plasmid encodes other genes which are outside of the T-DNA region and are necessary for the infection process. (See M. Holsters et al. (1980) Plasmid -3:212-230 for nopaline plasmids, and H. De Greve et al. (1981) Plasmid 6:235-248, D. J. Garfinkel and E. W. Nester (1980) J. Bacteriol 144:732-743, and G. Ooms (1980) J. Bacteriol 144:82-91 for octopine plasmids). Most important are the onc genes, which when mutated result in Ti plasmids incapable of oncogenicity. (These loci are also known as vir, for virulence.) Several onc genes have been accurately mapped and have been found to be located in regions conserved among various Ti plasmids (H. J. Klee et al. (1983) J. Bacteriol. 153:878-883, V. N. Iyer et al. (1982) Mol. Gen. Genet. 188:418-424). The onc genes function in trans, being capable of causing the transformation of plant cells with T-DNA of a different plasmid type and physically located on another plasmid (J. Hille et al. (1982) Plasmid 7:107-118, H. J. Klee et al. (1982) J. Bacteriol 150:327-331, A. J. de Framond et al. (1983) Biotechnol. 1:262-269). Nopaline Ti DNA has direct repeats of about 25 base pairs immediately adjacent to the left and right borders of the T-DNA which might be involved in either excision from the Ti plasmid or integration into the host genome (N. S. Yadav et al. (1982) Proc. Natl. Acad. Sci. USA 79:6322-6326), and a homologous sequence has been observed adjacent to an octopine T-DNA border (R. B. Simpson et al. (1982) Cell 29:1005-1014). Opine catabolism is specified by the occ and noc genes, respectively, of octopine- and nopaline-type plasmids. The Ti plasmid also encodes functions necessary for its own reproduction including an origin of replication. Ti plasmid transcripts have been detected in A tumefaciens cells by S. B. Gelvin et al. (1981) Plasmid 6:17-29, who found that T-DNA regions were weakly transcribed along with non-T-DNA sequences. Ti plasmid-determined characteristics have been reviewed by Merlo, supra (see especially Table II), and Ream and Gordon supra.

TIP Plasmid DNA

Different octopine-type Ti plasmids are nearly 100% homologous to each other when examined by DNA hybridization (T. C. Currier and E. W. Nester (1976) J. Bacteriol. 126:157-165) or restriction enzyme analysis (D. Sciaky et al. (1978) Plasmid 1:238-253). Nopaline-type Ti plasmids have as little as 67% homology to each other (Currier and Nester, supra). A survey revealed that different Ri plasmids are very homologous to each other (P. Costantino et al. (1981) Plasmid 5:170-182). N. H. Drummond and M.-D. Chilton (1978) J. Bacteriol. 136:1178-1183, showed that proportionally small sections of octopine- and nopaline-type Ti plasmids were homologous to each other. These homologies were mapped in detail by G. Engler et al. (1981) J. Mol. Biol. 152:183-208. They found that three of the four homologous regions were subdivided into three (overlapping the T-DNA), four (containing some onc genes), and nine (having onc genes) homologous sequences. The uninterrupted homology contains at least one tra gene (for conjugal transfer of the Ti plasmid to other bacterial cells), and genes involved in replication and incompatibility. This uninterrupted region has homology with a Sym plasmid (involved in symbiotic nitrogen fixation) from a species of Rhizobium, a different genus in the family Rhizobiaceae (R. K. Prakash et al. (1982) Plasmid 7:271-280). The order of the four regions is not conserved, though they are all oriented in the same direction. Part of the T-DNA sequence is very highly conserved between nopaline and octopine plasmids (M.-D. Chilton et al. (1978) Nature 275:147-149, A. Depicker et al. (1978) Nature 275:150-153). Ri plasmids have been shown to have extensive homology among themselves, and to both octopine (F. F. White and E. W. Nester (1980) J. Bacteriol. 144:710-720) and nopaline (G. Risuleo et al. (1982) Plasmid 7:45-51) Ti plasmids, primarily in regions encoding onc genes. Ri T-DNA contains extensive though weak homologies to T-DNA from both types of Ti plasmid (L. Willmitzer et al. (1982) Mol. Gen. Genet. 186:16-22). Plant DNA from uninfected Nicotiana glauca contains sequences, referred to as cT-DNA (cellular T-DNA), that show homology to a portion of the Ri T-DNA (F. F. White et al. (1983) Nature 301:348-350, L. Spano et al. (1982) Plant Molec. Biol. 1:291-300). G. A. Huffman et al. (1983) J. Bacteriol., have mapped the region of cross-hybridization and have shown that Ri plasmid, pRiA4b, is more closely related to a pTiA6 (octopine-type) than pTiT37 (nopaline-type) and that this Ri plasmid appears to carry sequence homologous to tms but not tmr. Their results also suggested that Ri T-DNA may be discontinuous, analogous to the case with octopine T-DNA.

It has been shown that a portion of the Ti (M.-D. Chilton et al. (1977) Cell 11:263-271) or Ri (M.-D. Chilton (1982) Nature 295:432-434, F. F. White et al. (1982) Proc. Natl. Acad. Sci. USA 79:3193-3197, L. Willmitzer (1982) Mol. Gen. Genet. 186:16-22) plasmid is found in the DNA of tumorous plant cells. The transferred DNA is known as T-DNA. T-DNA is integrated into the host DNA (M. F. Thomashow et al. (1980) Proc. Natl. Acad. Sci. USA 77:6448-6452, N. S. Yadav et al. (1980) Nature 287:458-461) at multiple sites (D. Ursic et al. (1983) Mol. Gen. Genet. 190:494-503, J. Memelink et al. (1983) Mol. Gen. Genet. 190:516-522) in the nucleus (M. P. Nuti et al. (1980) Plant Sci. Lett. 18:1-6, L. Willmitzer et al. (1980) Nature 287:359-361, M.-D. Chilton et al. (1980) Proc. Natl. Acad. Sci. USA 77:4060-4064). Much non-T-DNA Ti plasmid DNA appears to be transferred into the plant cell prior to T-DNA integration (H. Joos et al. (1983) EMBO J. 2:2151-2160).

M. F. Thomashow et al. (1980) Proc. Natl. Acad. Sci. USA 77:6448-6452, and M. F. Thomashow et al. (1980) Cell 19:729-739, found the T-DNA from octopine-type Ti plasmids to have been integrated in two separate sections, $T_L$-DNA and $T_R$-DNA, left and right T-DNAs respectively. The copy numbers of $T_R$ and $T_L$ can vary in different tumor lines (D. J. Merlo et al. (1980) Molec. Gen. Genet. 177:637-643). A core of T-DNA is highly homologous to nopaline T-DNA (Chilton et al. (1978) supra, and Depicker et al. (1978) supra), is required for tumor maintenance, is found in $T_L$, is generally present in one copy per cell, and codes for the genes tms, tmr, and tml. On the other hand, $T_R$ can be totally dispensed with (M. De Beuckeleer et al. (1981) Molec. Gen. Genet. 183:283-288, G. Ooms et al. (1982) Cell 30:589-597), though it is usually found in a high copy number (Merlo et al. (1980) supra). G. Ooms et al. (1982) Plasmid 7:15-29, hypothesized that $T_R$ is involved in T-DNA integration, though they find that when $T_R$ is deleted from the Ti plasmid, A. tumefaciens does retain some virulence. G. Ooms et al. (1982) Cell 30:589-597, showed that though T-DNA is occasionally deleted after integration in the plant genome, it is generally stable and that tumors containing a mixture of cells which differ in T-DNA organization are the result of multiple transformation events. The ocs gene is found in $T_L$ but can be deleted from the plant genome without loss of phenotypes related to tumorous growth. The left and right borders of $T_L$ and the left and right border of $T_R$ are designated herein as $T_LLB(A)$, $T_LRB(B)$, $T_RLB(C)$, and $T_RRB(D)$, respectively, have been sequenced (R. F. Barker et al. (1983) Plant Mol. Biol. 2:335–350, and R. F. Barker and J. D. Kemp, U.S. patent application Ser. No. 532,280), are 24 base pair imperfect direct repeats of each other, and are homologous with direct repeats found at either end of nopaline T-DNA. Plant DNA flanking integrated $T_LLB(A)$ has been observed to be composed of repeats of T-DNA sequences which are in either direct or inverted orientations (R. B. Simpson et al. (1982) Cell 29:1005–1014). M. Holsters et al. (1983) Mol. Gen. Genet. 190:35–41, found $T_L$ to be integrated in tanden copies separated by a "linker" of about 400 bp originating from both plant and T-DNA sequences.

In contrast to the situation in octopine-type tumors, nopaline T-DNA is integrated into the host genome in one continuous fragment (M. Lemmers et al. (1980) J. Mol. Biol. 144:353–376, P. Zambryski et al. (1980) Science 209:1385–1391). Direct tandem repeats were observed. T-DNA of plants regenerated from teratomas had minor modifications in the border fragments of the inserted DNA (Lemmers et al., supra). Sequence analysis of the junction between the right and left borders revealed a number of direct repeats and one inverted repeat. The latter spanned the junction (Zambryski et al. (1980) supra). The left junction has been shown to vary by at least 70 base pairs while the right junction varies no more than a single nucleotide (P. Zambryski et al. (1982) J. Mol. Appl. Genet. 1:361–370). Left and right borders in junctions of tandem arrays were separated by spacers which could be over 130 bp. The spacers were of unknown origin and contained some T-DNA sequences. T-DNA was found to be integrated into both repeated and low copy number host sequences. H. Joos et al. (1983) Cell 32:1057–1067, have shown that virulence is not eliminated after deletion of one of either of the usual nopaline T-DNA border sequences.

Simpson et al. (1982) supra, and Zambryski et al. (1980) supra have suggested that the direct repeats in the border regions are involved in integration of T-DNA into plant DNA. That T-DNA having borders from two different Ti plasmids are less specifically integrated than are homologous borders supports this suggestion (G. Ooms et al. (1982) Plant Molec. Biol. 1:265–276).

N. S. Yadav et al. (1982) Proc. Natl. Acad. Sci. USA 79:6322–6326, have found a chi site, which in the bacteriophage λ augments general recombination in the surrounding DNA as far as 10 kilobases away, in a nopaline Ti plasmid just outside the left end of the T-DNA. R. B. Simpson et al. (1982) Cell 29:1005–1014, did not observe a chi sequence in an octopine Ti plasmid in an equivalent position. The significance of the chi in the Ti plasmid is not known.

Manipulations of the TIP Plasmids

As detailed in the section on Shuttle Vectors, technology has been developed for the introduction of altered DNA sequences into desired locations on a TIP plasmid. Transposons can be easily inserted using this technology (D. J. Garfinkel et al. (1981) Cell 27:143–153). J.-P. Hernalsteen et al. (1980) Nature 287:654–656, have shown that a DNA sequence (here a bacterial transposon) inserted into T-DNA in the Ti plasmid is transferred and integrated into the recipient plant's genome. M. Holsters et al. (1982) Mol. Gen. Genet. 185:283–289, have shown that a bacterial transposon (Tn7) inserted into T-DNA could be recovered in a fully functional and seemingly unchanged form after integration into a plant genome. Though insertion of foreign DNA has been done with a number of genes from different sources, to date foreign genes have not usually been expressed in plant cells under control of their own promoters. Sources of these genes include rabbit β-globin (C. H. Shaw et al. (1983) Gene 23:315–330), alcohol dehydrogenase (Adh) from yeast (K. A. Barton et al. (1983) Cell 32:1033–1043), AdhI (J. Bennetzen, unpublished) and zein from corn, interferon and globin from mammals, and the mammalian virus SV40 (J. Schell, unpublished). However, when the nopaline synthase gene was inserted into octopine T-DNA and transformed into plant tissue, it was found to be fully functional (C. L. Fink (1982) M.S. thesis, University of Wisconsin-Madison). The gene encoding phaseolin, the storage protein found in seeds of the bean *Phaseolus vulgaris* L., has been transferred into and expressed in sunflower tumors. Transcription started and stopped at the correct positions, and introns were post-transcriptionally processed properly (N. Murai et al. (1983) Science 222:476–482, and T. C. Hall et al., U.S. application Ser. No. 485,613, which is hereby incorporated by reference). A. Caplan et al. (1983) Science 222:815–821, assert that a 900 bp fragment of DNA from the 5'-upstream region of the pea ribulose-1,5-bisphosphate carboxylase small subunit gene is sufficient to confer light-inducible expression in tobacco to a bacterial chloramphenicol acetyltransferase structural gene.

Deletions can be generated in a TIP plasmid by several methods. Shuttle vectors can be used to introduce deletions constructed by standard recombinant DNA techniques. Deletions with one predetermined end can be created by the improper excision of transposons (B. P. Koekman et al. (1979) Plasmid 2:347–357, and G. Ooms et al. (1982) Plasmid 7:15–29). J. Hille and R. Schilperoot (1981) Plasmid 6:151–154, have demonstrated that deletions having both ends at predetermined positions can be generated by use of two transposons. The technique can also be used to construct "recombinant DNA" molecules in vivo. P. Zambryski et al. (1983) EMBO J. 2:2143–2150, report use of a vector, deleted for all nopaline T-DNA genes except nos and transcript a, which on tobacco promotes the formation of very small calli and leads to the regeneration of plants having normal morphology.

The nopaline synthase gene has been used for insertion of DNA segments coding for drug resistance that can be used to select for transformed plant cells. In plant cells, a bacterial kanamycin resistance gene from Tn5 is not transcribed under control of its own promoter (J. D. Kemp et al. (1983) in *Genetic Engineering: Applications to Agriculture*, (Beltsville Symp. Agric. Res. 7), ed.: L. D. Owens, pp. 215–228; and C. L. Fink (1982) supra). M. W. Bevan et al. (1983) Nature 304:184–187, R. T. Fraley et al. (1983) Proc. Natl. Acad. Sci. USA 80:4803–4807, and L. Herrera-Estrella et al. (1983) EMBO J. 2:987–995, have inserted the kanamycin resistance gene (neomycin phosphotransferase II) from Tn5 behind (i.e. under control of) the nopaline synthase promoter. The construction was used to transform plant cells which in culture displayed resistance to kanamycin and its analogs such as G418. Herrera-Estrella et al., supra, reported a similar construction, in which a methotrexate resistance gene (dihydrofolate reductase) from Tn7 was placed behind the nopaline synthase promoter. Transformed cells were resistant to methotrexate, an antagonistic analog of folic acid. Similarly, L. Herrera-Estrella et al. (1983) Nature 303:209-213, have obtained expression in plant cells of enzymatic activity for octopine synthase and chloramphenicol acetyltransferase, an enzyme which in bacteria confers resistance to chloramphenicol, by placing the structural genes for these two enzymes under control of nos promoters.

N. Murai et al. (1983) Science 222:476-482, and T. C. Hall et al., U.S. application Ser. No. 485,614, which is hereby incorporated by reference, report the fusion of the ocs promoter and the 5'-end of the octopine synthase structural gene to the structural gene for the bean seed protein phaseolin. A fusion protein having the amino terminus of octopine synthase and lacking the amino terminus of phaseolin was produced under control of the T-DNA promoter. The introns, which were contributed by the phaseolin sequences, were posttranscriptionally processed properly.

A. J. de Framond et al. (1983) Biotechnol. 1:262-269, has reported that on the construction a "mini-Ti plasmid". In the nopaline T-DNA there is normally only one site cut by the restriction enzyme KpnI. A mutant lacking the site was constructed and a KpnI fragment, containing the entire nopaline T-DNA, was isolated. This fragment together with a kanamycin resistance gene was inserted into pRK290, thereby resulting in a plasmid which could be maintained in *A. tumefaciens* and lacked almost all non-T-DNA Ti sequences. By itself, this plasmid was not able to transform plant cells. However when placed in an *A. tumefaciens* strain containing an octopine Ti plasmid, tumors were induced which synthesized both octopine and nopaline. The mini-Ti plasmids has also been transferred into plant cells when complemented with a Ti plasmid deleted for its own T-DNA. These results indicated that the non-T-DNA functions acted in trans with T-DNA, that the missing nopaline Ti plasmid functions were complemented by the octopine Ti plasmid, and that the nopaline "mini-Ti" was functional in the transformation of plant cells. A similar pair of complementing plasmids, each containing either octopine T-DNA or onc genes, has been constructed by A. Hoekema et al. (1983) Nature 303:179-180.

Chilton et al. (Jan. 18, 1983) 15th Miami Winter Symp., reported on the construction of a "micro-Ti" plasmid made by resectioning the mini-Ti with SmaI to delete essentially all of T-DNA but the nopaline synthase gene and the left and right borders. The micro-Ti was inserted into a modified pRK290 plasmid that was missing its SmaI site, and was employed in a manner similar to mini-Ti, with comparable results. G. A. Dahl et al., U.S. patent application Ser. No. 532,280, disclose micro-Ti plasmids carrying ocs genes constructed from the $T_L$ region of the octopine-type plasmid pTi15955.

SUMMARY OF THE INVENTION

One object of this invention is to provide means for promoting the expression of structural genes within both plant cells and bacterial cells wherein said genes are foreign to said cells and would not be expressed otherwise. In pursuance of this goal, a dual-purpose promoter region/foreign structural gene combination is provided, which is a DNA sequence capable of controlling structural gene transcription within plant and bacterial cells combined with a structural gene which confers an identifiable phenotype to a cell transformed by the combination. Another object is to provide specialized plant tissues and plants having within them proteins encoded by foreign structural genes and, in cases where the protein is an enzyme, having or lacking metabolites or chemicals which respectively are not or are otherwise found in the cells in which the genes is inserted. Other objects include providing means for preliminarily testing and otherwise screening in prokaryotes constructions designed for eukaryotic expression, and providing means whereby transformed cells, both eukaryotic and prokaryotic, may be identified. Further objects and advantages will become evident from the following description.

The invention disclosed herein provides a plant comprising a genetically modified plant cell having a foreign structural gene introduced and expressed therein under control, in the preferred embodiment, of a T-DNA 1450bTx-derived plant expressible transcriptional control sequence. Further, the invention provides plant tissue comprising a plant cell having a genome comprising a foreign structural gene inserted in such orientation and spacing with respect to T-DNA-derived plant expressible transcriptional control sequences as to be expressible in the plant cell under control of those sequences. Also provided are novel strains of bacteria containing and replicating T-DNA, the T-DNA being modified to contain an inserted foreign structural gene in such orientation and spacing with respect to a T-DNA-derived plant and bacterium expressible promoter region as to be expressible in a plant or bacterial cell under control of said promoter region. Additionally, the invention provides novel vectors useful in efforts to transform plants having the ability to replicate in bacteria and comprising T-DNA, and further comprising a foreign structural gene inserted within T-DNA contained within the vector, in such manner as to be expressible in a plant cell or a bacterium under control of the T-DNA-derived promoter region. Furthermore, strains of bacteria harboring said vectors are disclosed.

The experimental work presented herein describes a DNA molecule having promoter activities that cause transcription both in eukaryotes and prokaryotes of a single copy of a structural gene. The availability of dual-purpose promoter region/foreign structural gene combinations will facilitate those of ordinary skill in the art of plant transformation to express foreign structual genes and to engage in other manipulations of DNA sequences. The ability to express a foreign structural gene in a prokaryote before transformation into a eukaryote permits one to functionally test a recombinant DNA construction towards ascertaining whether said construction has been properly assembled. Further utility of this promoter region is evident when it is used to control expression of a genetic marker. When the marker provides a resistance or tolerance to a selective agent, e.g. an antibiotic, that is toxic to both plant and bacterial cells, a single DNA sequence comprising the promoter region and the foreign structural gene can be used to identify or select transformed cells, whether such cells are bacteria or are from plants. Dual-purpose promoter region/structural gene combinations are especially useful where the combination is the sole means for expression in a cell of an identifiable phenotype conferred by the structural gene. Use of a single DNA sequence for two purposes, selection (or screening) in plants and selection (or screening) in bacteria, enables one to decrease the size of DNA molecules which carry such marker, thereby facilitating recombinant DNA manipulations and cell transformation processes.

The present invention comprises foreign structural genes under control of a dual-purpose promoter region and a polyadenylation site, said promoter/gene/polyadenylation site combination being inserted into a cell by any means known to the art. More specifically, in its preferred embodiment the invention disclosed herein further comprises expression in plant and bacterial cells of foreign structural genes under control of a certain T-DNA-derived plant expressible transcriptional control sequence, the 1450bTxPR, after introduction via T-DNA, that is to say, by inserting the foreign structural gene into T-DNA under control of the 1450bTxPR and ahead of a polyadenylation site and introducing the T-DNA containing the insert into a plant cell using known means. Once plant cells expressing a foreign structural gene under control of a dual-purpose promoter region are obtained, plant tissues and whole plants can be regenerated therefrom using methods and techniques well known in the art. The regenerated plants are then reproduced by conventional means and the introduced genes can be transferred to other strains and cultivars by conventional plant breeding techniques. The invention in principle applies to any introduction of a foreign structural gene into any plant species into which foreign DNA (in the preferred embodiment T-DNA) can be introduced by any means and in which said DNA can remain stably replicated. In general, these taxa presently include, but are not limited to, dicotyledenous plants such as sunflower (family Compositeae), tobacco (family Solanaceae), alfalfa, soybeans, and other legumes (family Leguminoseae), cotton (family Malvaceae), and most vegetables.

The invention is useful for genetically modifying bacteria, plant cells, plant tissues, and whole plants by inserting useful structural genes from other species, organisms, or strains. Such useful structural genes include, but are not limited to, genes conveying identifiable phenotypes such as the following: improved tolerance to extremes of heat or cold; improved tolerance to anaerobic conditions (e.g. water-logging), drought, or osmotic stress; improved resistance or tolerance to insect (e.g. insecticidal toxins such as the *Bacillus thuringiensis* crystal protein), arachnid, nematode, or epiphyte pests and fungal, bacterial, or viral diseases; the production of enzymes or secondary metabolites not normally found in said tissues or plants; improved nutritional (e.g. lectins and storage proteins such as zein or phaseolin), flavor (e.g. sweet proteins such as thaumatin), or processing properties when used for fiber or human or animal food; changed morphological traits or developmental patterns (e.g. leaf hairs which protect the plant from insects, coloring which is aesthetically pleasing, changed plant growth habits, dwarf plants, reduced time needed for the plants to reach maturity, expression of a gene in a tissue or at a time that gene is not usually expressed, and the like); male sterility; improved photosynthetic efficiency (including lowered photorespiration); improved nitrogen fixation; improved uptake of nutrients; improved tolerance to herbicides (e.g. glyphosate or triazines); increased crop yield; improved competition with other plants; genetic markers novel to the genetically modified cell; and the like. Genetic markers can be used to improve germplasm identification by the presence of one or more characteristic nucleic acid sequences, proteins, gene products, or phenotypes however identified. Genetic markers can distinguish a genetically modified plant, plant cell, or bacterial cell of the present invention from plants, plant cells, or bacteria which are not so modified, to facilitate transfer of a genetically linked or cotransformed artificially introduced DNA sequence or phenotype by other (e.g. sexual) means to other genotypes, or to facilitate identification of plants protected by patents or by plant variety protection certificates. Resistance (or tolerance) in cell or tissue culture to selective agents (i.e. selectable markers) and markers that are readily identified during screening (e.g. screenable markers such as distinctive cell-surface antigens or enzymes, like β-galactosidase, that are readily recognized visually) are also useful genetic markers. The invention is exemplified by placing a structural gene, encoding neomycin phosphotransferase II (NPTII) from Tn5 and providing a phenotype of resistance to the effects of kanamycin and its analogs (a kan gene), under control of a promoter region which in nature controls expression of the 1450bTx. The promoter/kan combination can be used to detect and select cells transformed by the combination. Any DNA sequences linked to the combination may be selected for, both in eukaryotes and prokaryotes, and cells transformed by linked DNA sequences may therefore be identified, as will be understood by those in the art. The invention is further exemplified by placing a structural gene for lectin under control of the 1450bTx promoter region. Lectin is a nutritionally important *Phaseolus vulgaris* (bean) seed cotyledon protein. The introduction and expression of the lectin structural gene can be used to enhance the protein content and change the nutritional value of various crops. Other uses of the invention, exploiting the properties of other structural genes introduced into various plant species, will be readily apparent to those skilled in the art.

The present invention additionally includes sub-Ti plasmids having foreign structural genes transcribed under control of the 1450bTx promoter region. The use of sub-Ti plasmids containing the direct repeats involved in incorporation of the T-DNA into the plant genome and one or more opine synthesizing genes can have the following useful results: 1. onc genes can be deleted resulting in greater success of plant regeneration from transformed tissue cultures or protoplasts. 2. Opine synthesizing genes can be used to identify those plant cells and tissues which have incorporated the T-DNA (and therefore in addition any linked or cotransformed genes which have been inserted). 3. Plant cells can be transformed by only parts of $T_L$, only parts of $T_R$, or parts of both $T_L$ and $T_R$. Since multiple copies of $T_R$ can be found in a transformed plant genome and it is actively transcribed, deletion of all or part of $T_L$ can result in a high level of expression of foreign genes in the absense of various onc genes. 4. Sub-Ti plasmids are relatively small, thereby facilitating or eliminating many manipulations otherwise required during the process of plant transformation.

DETAILED DESCRIPTION OF THE INVENTION

Figure 2:
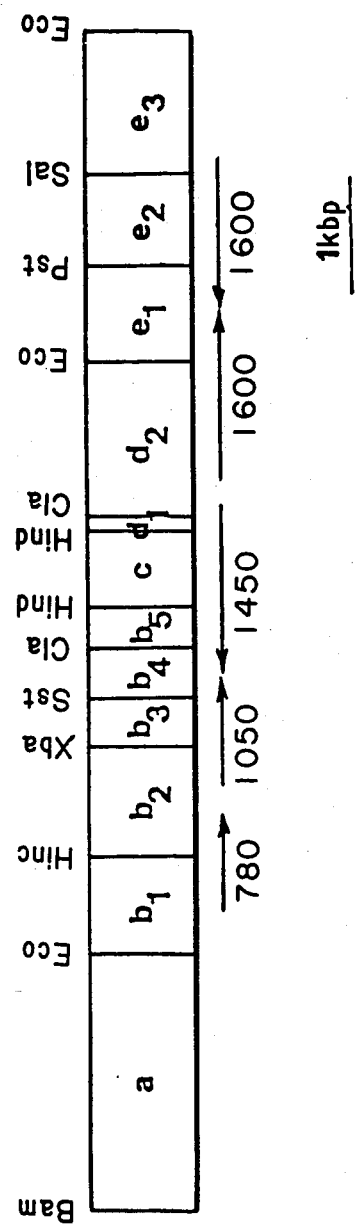
FIG. 2. is a restriction endonuclease map, taken from Karcher et al., supra, of $T_R$ indicating the map positions and polarities of five $T_R$ transcripts. The enzymes designated are BamHI, EcoRI, HincII, XbaI, SstI, ClaI, HindIII, PstI, and SalI. Not all sites within $T_R$ cut by the above enzymes are included in this map.

The following definitions are provided, in order to remove ambiguities to the intent or scope of their usage in the specification and claims.

Promoter: Refers to sequences at the 5'-end of a structural gene involved in initiation of transcription. The present invention is made up of two promoter activities, a eukaryotic promoter activity and a prokaryotic promoter activity, positioned within a promoter-bearing region of T-DNA sequence so as to cause transcription of any desired foreign structural gene DNA sequence in both eukaryotes and prokaryotes, in particular plants and gram-negative bacteria. In nature the T-DNA promoter region sequences exemplified herein causes transcription in crown gall tumors of the 1450bTx. Expression under control of a promoter may take the form of direct expression in which the structural gene normally controlled by the promoter is removed in part or in whole and replaced by the inserted foreign structural gene, a start codon being provided either as a remnant of the T-DNA structural gene or as part of the inserted structural gene, or by fusion protein expression in which part or all of the structural gene is inserted in correct reading frame phase within the exisiting T-DNA structural gene. In the latter case, the expression product is referred to as a fusion protein. Eukaryotic promoter sequences are commonly recognized by the presence of DNA sequences homologous to the canonical form 5' . . . TATAA . . . 3' about 10–30 base pairs (bp) 5' to the location of the 5'-end of the mRNA (cap site). About 30 bp 5' to the TATAA another promoter sequence is often found which is recognized by the presence of DNA sequences homologous to the canonical form 5' . . . CCAAT . . . 3'. Translational initiation is usually most efficient at the first 5' . . . AUG . . . 3' 3' from the cap site.

Polyadenylation site: Refers herein to any nucleic acid sequence capable of promoting polyadenylation of messenger RNA (mRNA) in eukaryotes, i.e. after transcriptional termination polyadenylic acid "tails" will be added to the 3'-end of a mRNA precursor. The polyadenylation site DNA segment may itself be a composite of segments derived from a plurality of sources, naturally occurring or synthetic, prokaryotic or eukaryotic, and may be from a genomic DNA or an mRNA-derived cDNA. Polyadenylation sites are commonly recognized by the presence of homology to the canonical form 5' . . . AATAAA . . . 3', although variations of distance 5' to the 3'-end of the transcript, partial "read-thru", and multiple tandem canonical sequences are not uncommon. It should be recognized that a canonical "polyadenylation site" may actually determine the location of the 3'-end of the mRNA and not polyadenylation per se (N. Proudfoot (1984) Nature 307:412–413).

Transcription controlling sequences: Refers to a promoter/polyadenylation site combination flanking a structural gene. The promoter and polyadenylation DNA sequences flanking a particular foreign structural gene need not be derived from the same source genes (e.g. pairing two different T-DNA transcripts) or the same taxonomic source (e.g. pairing sequences from T-DNA with sequences from non-T-DNA sources such as plants, animals, fungi, yeasts, eukaryotic viruses, bacteria, and synthetic sequences).

Foreign structural gene: As used herein includes that portion of a gene comprising a DNA segment coding for a foreign RNA, protein, polypeptide or portion thereof, possibly including a translational start codon. A foreign structural gene may encode a gene product not normally found in the cell in which the gene is introduced. Additionally, the term refers to artificially introduced copies of a structural gene otherwise naturally found within the cell. A foreign structural gene may be derived in whole or in part from prokaryotic DNA, eukaryotic DNA, episomal DNA, plasmid DNA, plastid DNA, genomic DNA, cDNA, viral DNA, viral cDNA, chemically synthesized DNA, or the like. It is further contemplated that a foreign structural gene may contain one or more modifications in either the coding segments or untranslated regions which could affect the biological activity or chemical structure of the expression product, the rate of expression or the manner of expression control. Such modifications include, but are not limited to, mutations, insertions, deletions, and substitutions of one or more nucleotides, and "silent" modifications that do not alter the chemical structure of the expression product but which affect intercellular localization, transport, excretion or stability of the expression product. The structural gene may constitute an uninterrupted coding sequence or it may include one or more introns, bounded by the appropriate plant functional splice junctions, which may be obtained from synthetic or a naturally occurring source. The structural gene may be a composite of segments derived from a plurality of sources, naturally occurring or synthetic, coding for a composite protein, the composite protein being foreign to the cell into which the gene is introduced and expressed or being derived in part from a foreign protein. The foreign structural gene may be a fusion protein, and in particular, may be fused to all or part of a structural gene derived from that which the transcriptional control sequences were derived.

Dual-purpose promoter region/foreign structural gene combination: Refers herein to a foreign structural gene controlled by two or more promoter activites, e.g. a eukaryotic promoter activity and a prokaryotic promoter activity. The locations of the activities need not overlap, i.e. the eukaryotic and prokaryotic activities may or may not be physically separable. For instance, the eukaryotic activity and the prokaryotic activity may be localized to different DNA segments. The particular distance between the activities is not important for operation of the present invention as long as there are no prokaryotic transcriptional termination signals between the prokaryotic promoter activity and the structural gene and as long as no eukaryotic signals involved in mRNA termination are between the cap site and the coding sequence.

Plant tissue: Includes differentiated and undifferentiated tissues of plants including but not limited to roots, shoots, pollen, seeds, tumor tissue, such as crown galls, and various forms of aggregations of plant cells in culture, such as embryos and calluses. The plant tissue may be in planta or in organ, tissue, or cell culture.

Plant cell: As used herein includes plant cells in planta and plant cells and protoplasts in culture.

Bacterial cell: As used herein includes bacteria in culture, including but not limited to biologically pure cultures, and dispersed in the environment.

Figure 1:
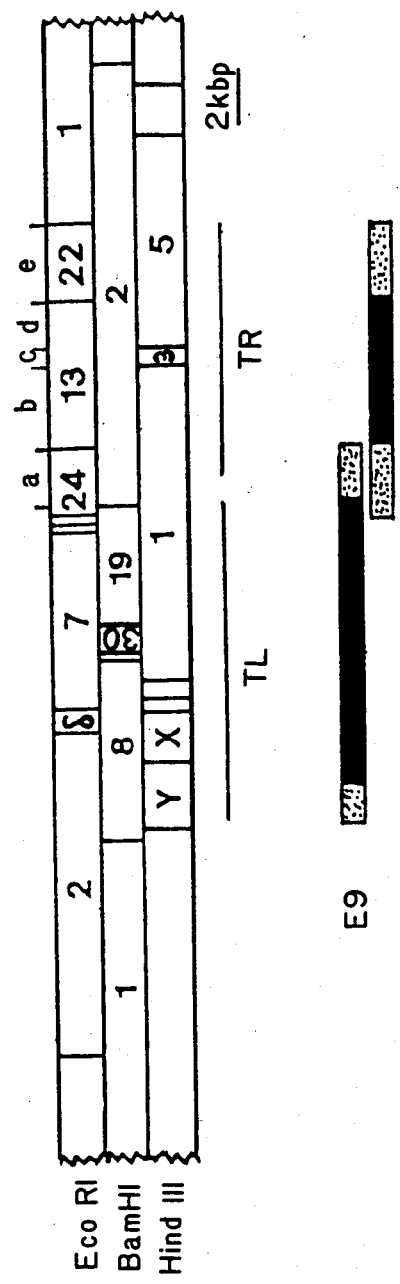
FIG. 1. is a restriction endonulcease map, taken from S. J. Karcher et al. (1984) Mol. Gen. Genet., of the T-DNA region of a typical octopinetype Ti-plasmid. BamHI fragment 30' is positioned between BamHI fragments 8 and 30. Bars beneath the map indicate the regions of DNA maintained in the E9 tobacco tumor lines used.

DNA fragment designations are defined in FIGS. 1 and 2.

Production of a genetically modified cell expressing a dual-purpose promoter region/foreign structural gene combination combines the specific teachings of the present disclosure with a variety of techniques and expedients known in the art. In most instances, alternative expedients exist for each stage of the overall process. The choice of expedients depends on variables such as the choice of the basic vector system for the introduction and stable maintenance of the dual-purpose combination, the plant species to be modified and the desired regeneration strategy, and the particular foreign structural gene or promoter sequences to be used, all of which present alternative process steps which those of ordinary skill are able to select and use to achieve a desired result. For instance, although the starting point for obtaining a dual-purpose promoter region is exemplified in the present application by T-DNA isolated from pTiA6, DNA sequences of other homologous Ti plasmids might be substituted as long as appropriate modifications are made to the promoter region isolation and manipulation procedures. (Often, pTi15955 may be used without modification.) Dual-purpose promoter regions other than that derived from the 1450bTx gene taught herein may be discovered or constructed. Homologous genes may be identified by those of ordinary skill in the art by the ability of homologous nucleic acids to cross-hybridize under conditions of appropriate stringency or by comparison of nucleic acid or protein sequences, as is well understood in the art. It will be understood that there may be minor sequence variations within gene sequences utilized or disclosed in the present application. These variations may be determined by standard techniques to enable those of ordinary skill in the art to manipulate and bring into utility the promoter regions of such homologous genes. As novel means are developed for the stable insertion of foreign genes in plant cells, those of ordinary skill in the art will be able to select among those alternate process steps to achieve a desired result. The fundamental aspects of the invention are the nature of the dual-purpose promoter region and its use to drive expression of a single copy of a foreign structural gene in both prokaryotes and eukaryotes. Other aspects include the nature and structure of the foreign structural gene and its means of insertion and expression in bacterial and plant genomes. The remaining steps of the preferred embodiment for obtaining a genetically modified plant include inserting the 1450bTxPR/structural gene combination into T-DNA, monitoring expression in bacteria, transferring the modified T-DNA to a plant cell wherein the modified T-DNA becomes stably integrated as part of the plant cell genome, techniques for in vitro culture and eventual regeneration into whole plants, which may include steps for selecting and detecting transformed plant cells and steps of transferring the introduced gene, and other linked or cotransformed DNA sequences from the originally transformed strain into commercially acceptable cultivars, and monitoring expression in transformed plants.

A principal feature of the present invention in its preferred embodiment is the construction of a T-DNA derivative having an inserted foreign structural gene under control of the 1450bTxPR, i.e., between a dual-purpose promoter region and a polyadenylation site, as these terms have been defined, supra. The structural gene must be inserted in correct position and orientation with respect to the promoter region. Position has two aspects. The first relates to which side of the promoter the structural gene is inserted. It is known that the majority of promoters control initiation of transcription and translation in one direction only along the DNA. The region of DNA lying under promoter control is said to lie "downstream" or alternatively "behind" or "3' to" the promoter. Therefore, to be controlled by the promoter, the correct position of foreign structural gene insertion must by "downstream" from the promoter. The second aspect of position refers to the distance, in base pairs, between known functional elements of the promoter, for example the transcription initiation site, and the translational start site of the structural gene. Substantial variation appears to exist with regard to this distance, from promoter to promoter. Therefore, the structural requirements in this regard are best described in functional terms. As a first approximation, reasonable operability can be obtained when the distance between the promoter and the inserted foreign structural gene is similar to the distance between the promoter and the gene it normally controls. Orientation refers to the directionality of the structural gene. That portion of a structural gene which ultimately codes for the amino terminus of the foreign protein is termed the 5'-end of the structural gene, while that end which codes for amino acids near the carboxyl end of the protein is termed the 3'-end of the structural gene. Correct orientation of the foreign structural gene is with the 5'-end thereof proximal to the promoter. An additional requirement in the case of constructions leading to fusion protein expression is that the fusion of two structural genes must be such that the coding sequences of the two genes are in the same reading frame phase, a structural requirement which is well understood in the art. An exception to this phasing requirement exists in the case where an intron separates coding sequences derived from the two structural genes. In that case, both structural genes must be provided with compatible splice sites, and the intron splice sites must be so positioned that the correct reading frame is restored in phase after the intron is removed by post-transcriptional processing. Differences in rates of expression or developmental control may be observed when different foreign structural genes are inserted under control of the 1450bTxPR derivative or other dual-purpose promoter regions. Rates of expression may also be greatly influenced by the details of the resultant mRNA's secondary structure, especially stem-loop structures. As is well understood in the art, translational rates in prokaryotic cells will be affected by the presence of a ribosomal RNA binding sequence 5' to the AUG translational start site (J. Shine and L. Dalgarno (1974) Proc. Natl. Acad. Sci. USA 71:1342–1346), and translational rates in eukaryotic cells may be affected by the particular nucleotides flanking the AUG (M. Kozak (1981) Nucl. Acids Res. 9:5233–5252). Different properties, including, but not limited to, such properties as stability, intercellular or intracellular localization or excretion, solubility, target specificity, and other functional properties of the expressed protein itself may be observed in the case of fusion proteins depending upon the insertion site, the length and properties of the segments of the foreign proteins included within the fusion protein, and effects on folded configuration thereof, all of which present numerous opportunities to manipulate and control the functional properties of the foreign protein product, depending upon the desired physiological properties within the plant cell, plant tissue, and whole plant. Similarly to the promoter region, the polyadenylation site must be located in correct position and orientation relative to the 3'-end of the coding sequence. Fusion proteins are also possible between the 3'-end of the foreign structural gene protein and a polypeptide encoded by the DNA which serves as a source of the polyadenylation site.

As will be understood by persons skilled in the art, other sites may be substituted for the ClaI promoter/structural gene suture utilized in the preferred embodiment provided that the sequence at the junction remains compatible with translational and transcriptional functions. The restriction sites at the 5'- and 3'-ends of the structural gene-bearing fragment may be identical or different. Use of sites having sticky-ends of different specificities at the two ends of the gene fragment will automatically correctly orient the structural gene behind the 1450bTxPR. When restriction sites have incompatible ends, they may be converted to blunt-ends by methods well known in the art and blunt-end ligated together. Use of appropriate linkers, adapters, or couplers will also be advantageous in certain circumstances for forming a junction between the 1450bTxPR and a structural gene, as will be evident to those of ordinary skill in the art, and is exemplified herein.

Persons practicing the art of plant transformation will be aware of numerous situations where structural genes are advantageously expressed in bacterial hosts as well as in plant cells. However, use of the 1450bTxPR to drive expression of genes that function as genetic markers for identification and/or selection of transformed cells is particularly advantageous and is exemplified herein (Example 4). Transformation of cells, whether prokaryotic or eukaryotic, is most easily accomplished when one has a means for readily identifying cells transformed by a particular recombinant DNA molecule carrying the marker and linked DNA sequences. Use of the 1450bTxPR to effect expression of a single marker saves those of ordinary skill the trouble of inserting a second marker into a transformation vector. Additionally, lack of a second marker allows construction of transformation vectors smaller than would be otherwise possible, thereby facilitating DNA manipulations, increasing transformation efficiencies, and the like. However, when a particular marker is placed behind the 1450bTxPR, one must be aware of homologous sequences elsewhere in a plasmid that may lead to genetic rearrangements, as is well understood in the art. For example, a kan gene used to select for homogenotes deleted for $T_L$ onc genes and a 1450bTxPR/kan combination in $T_R$ can recombine, resulting in deletion or inversion of the intervening T-DNA sequences. Similar considerations require that care must be taken when more than one copy of the 1450bTxPR is used to drive expression of a similar number of diverse foreign structural genes.

As will be apparent to those of ordinary skill in the art, the dual-purpose promoter region/foreign structural gene combination may be placed between any restriction sites convenient for removing the combination from the plasmid it is carried on and convenient for insertion into the plant transformation or shuttle vector of choice. Location of the dual-purpose combination insertion site within T-DNA is not critical as long as the transfer function of sequences immediately surrounding the T-DNA borders are not disrupted, since in prior art studies these regions appear to be essential for insertion of the modified T-DNA into the plant genome. Preferred insertion sites are those which lie in areas that are most actively transcribed, in particular $T_R$, and especially a region including the 1450bTx. The T-DNA into which the dual-purpose combination is inserted is obtained from any of the TIP plasmids, and the combination is inserted by standard techniques well known to those skilled in the art. The orientation of the inserted dual-purpose combination, with respect to the direction of transcription and translation of endogenous T-DNA or vector genes is not critical, either of the two possible orientations is functional. Differences in rates of expression in plants may be observed when a given gene is inserted at different locations within T-DNA, possibly because of such factors as DNA methylation and chromatin structure.

A convenient means for inserting a dual-purpose combination and any desired linked DNA into T-DNA involves the use of a shuttle vector, as described in the Background, having segments of T-DNA (those segments between which insertion is desired) incorporated into a plasmid capable of replicating in *E. coli*. The T-DNA segment contains a restriction site, preferably one which is unique within the shuttle vector. The dual-purpose combination can be inserted at the unique site in the T-DNA sequence and the shuttle vector is transferred into cells of the appropriate Agrobacterium strain, preferably one whose T-DNA is homologous with the T-DNA segments of the shuttle vector. The transformed Agrobacterium strain is preferably grown under conditions which permit selection of a double-homologous recombination (homogenotization) event which results in replacement of a pre-existing segment of the Ti plasmid with a segment of T-DNA of the shuttle vector. However, it should be noted that the present invention is not limited to the introduction of the dual-purpose combination into T-DNA by a double homologous recombination mechanism; a single-homologous recombination (cointegration) event with a shuttle vector (perhaps having only a single continuous region of homology with the T-DNA) at a single site or an insertion of a promoter region/structural gene-carrying bacterial transposon will also prove an effective means for inserting that combination into T-DNA.

Following the strategy just described, the modified T-DNA can be transferred to plant cells by any technique known in the art. For example, this transfer is most conveniently accomplished either by direct infection of plants with the novel Agrobacterium strain containing a foreign structural gene incorporated within T-DNA, or by cocultivation of the Agrobacterium strain with plant cells. The former technique, direct infection, results in due course in the appearance of a tumor mass or crown gall at the site of infection. Crown gall cells can be subsequently grown in culture and, under appropriate circumstances known to those of ordinary skill in the art, regenerated into whole plants that contain the inserted T-DNA segment. Using the method of cocultivation, a certain proportion of the plant cells are transformed, that is to say have T-DNA transferred therein and inserted in the plant cell genome. In either case, the transformed cells must be selected or screened to distinguish them from untransformed cells. Selection is most readily accomplished by providing a selectable marker incorporated into the T-DNA in addition to the foreign structural gene. Published examples of markers include either a methotrexate-resistant dihydrofolate reductase or neomycin phosphotransferase II (NPTII) expresssed under control of a nopaline synthase promoter. These markers are selected by growth in medium containing methotrexate or kanamycin, respectively, or their analogs. The toxic effect of heavy metal ions can be lessened by the presence of metallothionein. Indeed, the present invention is exemplified by construction of a selectable marker, a 1450bTxPR/NPTII structural gene combination, suitable for selection of transformed plant tissues. In addition, the T-DNA provides endogenous markers such as gene(s) controlling hormone-independent growth of Ti-induced tumors in culture, gene(s) controlling abnormal morphology of Ri-induced tumor roots, and gene(s) that control resistance to toxic compounds such as amino acid analogs, such resistance being provided by an opine synthesizing enzyme (e.g. ocs). Screening methods well known to those skilled in the art include, but are not limited to, assays for opine production, specific hybridization to characteristic nucleic acid sequences, or immunological assays for specific proteins, including ELISAs (an acronym for "enzyme linked immunosorbant assay"), radioimmune-assays and "western" blots. Additionally the phenotype of expressed foreign gene can be used to identify transformed tissue (e.g. resistance to antibiotics or insecticidal properties of the *B. thuringiensis* crystal protein).

An alternative to the shuttle vector strategy involves the use of plasmids comprising T-DNA or modified T-DNA, into which a dual-purpose combination is inserted, said plasmids being capable of independent replication in an Agrobacterium strain. Recent evidence reviewed in the Background indicates that the T-DNA of such plasmids can be transferred from an Agrobacterium strain to a plant cell provided the Agrobacterium strain contains certain trans-acting genes whose function is to promote the transfer of T-DNA to a plant cell. Plasmids that contain T-DNA and are able to replicate independently in an Agrobacterium strain are herein terred "sub-TIP" or sub-Ti plasmids. A spectrum of variations is possible in which the sub-TIP plasmids differ in the amount of T-DNA they contain. One end of the spectrum retains all of the T-DNA from the TIP plasmid, and is sometimes termed a "mini-TIP" or mini-Ti plasmid. At the other end of the spectrum, all but an amount of DNA surrounding the T-DNA borders is deleted, the remaining portions being the minimum necessary for the sub-TIP plasmid to be transferrable and integratable in the host cell. Such plasmids are termed "micro-TIP" or micro-Ti. Sub-TIP plasmids are advantageous in that they are small and relatively easy to manipulate directly, eliminating the need to transfer the gene to T-DNA from a shuttle vector by homologous recombination. After the desired structural gene has been inserted, they can easily be introduced directly into a Agrobacterium cell containing the trans-acting vir genes that promote T-DNA transfer. Introduction into an Agrobacterium strain is conveniently accomplished either by transformation of the Agrobacterium strain or by conjugal transfer from a donor bacterial cell, the techniques for which are well known to those of ordinary skill. For purposes of introduction of novel DNA sequences into a plant genome, TIP plasmids and sub-TIP plasmids should be considered functionally equivalent. Example 6 discloses sub-Ti plasmids, generally based on $T_R$, and discusses some more detailed considerations.

Although the preferred embodiment of this invention incorporates a T-DNA-based Agrobacterium-mediated system for incorporation of the dualpurpose promoter region/foreign structural gene combination into the genome of the plant which is to be transformed, other means for transferring and incorporating the combination are also included within the scope of this invention. Other means for the stable incorporation of the dualpurpose combination into a plant genome additionally include, but are not limited to, use of vectors based upon viral genomes, minichromosomes, transposons, and homologous or nonhomologous recombination into plant chromosomes. Alternate forms of delivery of these vectors into a plant cell additionally include, but are not limited to, fusion with vectorcontaining liposomes or bacterial spheroplasts, microinjection, encapsidation in viral coat protein followed by an infection-like process, and direct uptake of DNA, possibly after induction of plasmalemma permeability by an electric pulse, a laser, or a chemical agent. Means for transient incorporation and/or expression are also included within the scope of this invention. Systems based on Agrobacterium cells and TIPs can be used to transform dicots by transfer of DNA from a bacterium to a plant cell; systems based on alternate vectors or means for vector delivery may be used to transform all gymnosperms and all angiosperms, including both monocots and dicots.

Regeneration of transformed cells and tissues is accomplished by resort to known techniques. An object of the regeneration step is to obtain a whole plant that grows and reproduces normally but which retains integrated T-DNA. The techniques of regeneration vary somewhat according to principles known in the art, depending upon the origin of the T-DNA, the nature of any modifications thereto and the species of the transformed plant. Plant cells transformed by an Ri-type T-DNA are readily regenerated, using techniques well known to those of ordinary skill, without undue experimentation. Plant cells transformed by Ti-type T-DNA can be regenerated, in some instances, by the proper manipulation of hormone levels in culture. Preferably, however, the Ti-transformed tissue is most easily regenerated if the T-DNA has been mutated in one or both of the tmr and tms genes. Inactivation of these genes returns the hormone balance in the transformed tissue towards normal and greatly expands the ease and manipulation of the tissue's hormone levels in culture, leading to a plant that is readily regenerated because of its more normal hormone physiology. It is important to note that if the mutations in tmr and tms are introduced into T-DNA by double homologous recombination with a shuttle vector, the incorporation of the mutation must be selected in a different manner than the incorporation of the dual-purpose promoter region/structural gene combination. For example, in the former instance one might select for tmr and tms inactivation by chloramphenicol resistance while the promoter region/foreign gene selection might be for resistance to kanamycin. The inactivation of the tms and tmr loci may be accomplished by an insertion, deletion, or substitution of one or more nucleotides within the coding regions or promoters of these genes, the mutation being designed to inactivate the promoter or disrupt the structure of the protein. (The construction of suitable mutations has been exemplified by T. C. Hall et al., U.S. application Ser. Nos. 485,613 and 485,614, and by references cited in the Background.) In some instances, tumor cells are able to regenerate shoots which carry integrated T-DNA and express T-DNA genes, such as nopaline synthase, and which also express an inserted plant structural gene. The shoots can be maintained vegetatively by grafting to rooted plants and can develop fertile flowers. The shoots thus serve as parental plant material for normal progeny plants carrying T-DNA and expressing the foreign structural gene inserted therein.

The genotype of the plant tissue transformed is often chosen for the ease with which its cells can be grown and regenerated in in vitro culture and for susceptibility to the selective agent to be used. Should a cultivar of agronomic interest be unsuitable for these manipulations, a more amenable variety is first transformed. After regeneration, the newly introduced dual-purpose promoter region/foreign structural gene combination and any linked and/or cotransformed DNA may be readily transferred to the desired agronomic cultivar by techniques well known to those skilled in the arts of plant breeding and plant genetics. Sexual crosses of transformed plants with the agronomic cultivars yield initial hybrids. These hybrids can then be back-crossed with plants of the desired genetic background. Progeny are continuously screened and/or selected for the continued presence of integrated foreign DNA or for a new phenotype resulting from expression of genes carried by the inserted foreign DNA. In this manner, after a number of rounds of back-crossing and selection, plants can be produced having a genotype essentially identical to the agronomically desired parents with the addition of inserted foreign DNA sequences.

EXAMPLES

The following Examples utilize many techniques well known and accessible to those skilled in the arts of molecular biology and manipulation of TIPs and Agrobacterium; such methods are fully described in one or more of the cited references if not described in detail herein. Enzymes are obtained from commercial sources and are used according to the vendor's recommendations or other variations known to the art. Reagents, buffers and culture conditions are also known to those in the art. Reference works containing such standard techniques include the following: R. Wu, ed. (1979) Meth. Enzymol. 68, R. Wu et al., eds. (1983) Meth. Enzymol. 100 and 101, L. Grossman and K. Moldave, eds. (1980) Meth. Enzymol. 65, J. H. Miller (1972) *Experiments in Molecular Genetics*, R. Davis et al. (1980) *Advanced Bacterial Genetics*, R. F. Schleif and P. C. Wensink (1982) *Practical Methods in Molecular Biology*, and T. Maniatis et al. (1982) *Molecular Cloning*. Additionally, R. F. Lathe et al. (1983) Genet. Engin. 4:1–56, make useful comments on DNA manipulations.

Textual use of the name of a restriction endonuclease in isolation, e.g. "BclI", refers to use of that enzyme in an enzymatic digestion, except in a diagram where it can refer to the site of a sequence susceptible to action of that enzyme, e.g. a restriction site. In the text, restriction sites are indicated by the additional use of the word "site", e.g. "BclI site". The additional use of the word "fragment", e.g. "BclI fragment", indicates a linear double-stranded DNA molecule having ends generated by action of the named enzyme (e.g. a restriction fragment). A phrase such as "BclI/SmaI fragment" indicates that the restriction fragment was generated by the action of two different enzymes, here BclI and SmaI, the two ends resulting from the action of different enzymes. Note that the ends will have the characteristics of being "sticky" (i.e. having a single-stranded protrusion capable of base-pairing with a complementary single-stranded oligonucleotide) or "blunt" and that the specificity of a sticky-end will be determined by the specificity of the enzyme which produces it.

Plasmids, and only plasmids, are prefaced with a "p", e.g., pTi15955 or pUC13, and strain designations parenthetically indicate a plasmid harbored within, e.g., *A. tumefaciens* (pTi15955) or *E. coli* JM83 (pUC13). The following strains are on deposit:

E. coli K12 RR1 (pRK290Kan-1)—NRRL B-15736
A. tumefaciens (pTi15955)—ATCC 15955
E. coli C600 (pKS4)—NRRL B-15394
E. coli HB101 (pPVL134)—ATCC 39181

Other plasmids and strains are widely available and accessible to those in the art.

EXAMPLE 1

This Example discloses and discusses results of transcript mapping experiments which located the 1450 base transcript (1450bTx) and also teaches the methods used to obtain said results. These experimental results are essentially excerpted from S. J. Karcher et al. (1984) Molec. Gen. Genet., and are included herein as background necessary to understand the present invention.

1.1 Results

FIG. 1 shows a restriction endonulcease map of part of pTiA6 indicating the regions of the Ti plasmid which are stably integrated into plant DNA (the T-DNA). Subfragments of BamHI fragment 2 (see map, FIG. 2) were cloned into the plasmids pBR325, pMK2004, or pUC13 and used as hybridization probes to localize RNAs, transcribed in plant tumors, encoded by the $T_R$ region of the T-DNA. A Northern blot analysis of total cellular RNA or polyA+ RNA isolated from the E9 suspension cell tumor line, a *Nicotiana tabacum* line incited by *A. tumefaciens* (pTiB$_6$806) well known in the art (M. F. Thomashow et al. (1980) Cell 19:729–739), revealed an RNA approximately 1450 bases in size that hybridized to probes $b_5$, c, and $d_1$. There may also have been a low level of hybridization of this RNA to probes $b_4$ and $b_3$ (FIG. 2).

To define more precisely the boundaries and the polarities of the 1450bTx, $S_1$ nuclease mapping experiments were performed. Fragments to be used as probes for $S_1$ nuclease protection experiments were cloned in both orientations into vectors derived from the single stranded bacteriophage M13 (see Example 1.3b). The use of such M13-derived single-stranded DNA had advantages over the use of double-stranded DNA as probes for $S_1$ nuclease analysis. Hybridization between DNA and RNA could be performed at 65° C. in an aqueous solution in a relatively short time. In addition, because cloning into M13 separates the strands of DNA from one another, each strand could be tested separately for protection from $S_1$ nuclease digestion by RNA. By determining which cloned DNA strand was protected and the orientation of the insert cloned into the M13 multiple cloning site, the polarity of transcription of the RNA could be inferred. When both strands of a given region were protected, transcription in both directions was indicated.

The results of such an analysis, using E9 total cellular RNA, are shown in FIG. 2. By using $d_1+d_2$ as an $S_1$ nuclease protection probe, it was determined that the 1450bTx begins about 240 bp to the right of the HindIII site between c and $d_1$. Both fragments c and $b_5$ were fully protected from $S_1$ nuclease digestion by this transcript. When $b_5$ was used as an $S_1$ nuclease protection probe, a fragment of about 280 bp was recovered. When $b_4+b_5$ was used, a fragment of approximately 20 bp more was protected from $S_1$ nuclease digestion. These data indicate that the 1450bTx terminates in $b_4$, just to the left of the ClaI site between $b_4$ and $b_5$.

1.2 Discussion

Using Northern blotting and $S_1$ nuclease analysis, five transcripts encoded by the $T_R$ region of the T-DNA from octopine-type crown gall tumors were localized. These polyadenylated RNAs were transcribed from internal T-DNA promoters and not from host plant promoters. Northern blot analysis indicated that in the E9 tumor line the most abundant transcripts encoded by $T_R$, including the 1450bTx, were considerably more abundant than those encoded by $T_L$. $T_R$ is therefore of interest for use in plant genetic engineering experiments since it contains strong promoters and yet is not directly involved in tumorigenesis.

An $S_1$ nuclease mapping procedure was used to determine the direction of transcription of these RNAs and to localize their 5' and 3' termini more precisely than is possible with blotting experiments. The $S_1$ nuclease protection data indicated that the gene encoding the 1450 base RNA does not contain any detectable intervening sequences. The transcript size determined by Northern blotting analysis was larger than the size indicated by the $S_1$ nuclease analysis. This difference in size is easily accounted for by the posttranscriptional addition of a poly(A) sequence.

The Northern blot and $S_1$ nuclease protection data corresponded well with DNA sequence data of this region derived by others (R. F. Barker et al. (1983) Plant Molec. Biol. 2:335–350, R. F. Barker and J. D. Kemp, U.S. patent application Ser. No. 553,786). There was an open reading frame (ORF24 therein) of the orientation and length predicted by the transcript mapping experiments described above. In addition, in the 1450bTxPR were sequences resembling the TATAA or Goldberg-Hogness box implicated in promotion of eukaryotic transcription (J. E. Darnell (1982) Nature 297:365–371). The TATAA box has been shown to be necessary for accurate in vitro transcription (B. Wasylyk et al. (1980) Proc. Natl. Acad. Sci. USA 77:7024–7028) but sequences upstream from TATAA are known to be required for efficient transcription in vivo. The sequence CCAAT is often found upstream from the TATAA box (C. Benoist et al. (1980) Nucleic Acids Res. 8:127–142, A. Efstratiadis et al. (1980) Cell 21:653–668, T. Shenk (1981) Curr. Topics Microbiol. Immunol. 93:25–46) and a homolog was present in the 1450bTxPR. Near the 3'-terminus of the transcript are three homologs of the hexanucleotide AATAAA, a sequence signal necessary for proper determination of the 3'-end of many eukaryotic mRNAs (N. Proudfoot (1984) Nature 307:412–413).

1.3 Materials and methods

1.3a Culture conditions

Crown gall tumor lines were grown at 25° C. under constant illumination on MS3 medium either without (for suspension cultures) or with (for callus cultures) 1.0% phytagar (M. F. Thomashow et al. (1980) Cell 19:729–739). The nontumorous tobacco line XSR, which was used for a control, was grown in MS3 medium supplemented with 1.0 mg/l naphthalene acetic acid and 0.1 mg/l benzylaminopurine.

*E. coli* strains harboring recombinant plasmids were grown in L broth supplemented with 0.2% casamino acids. Antibiotic concentrations used were for *E. coli*: ampicillin, 50–100 μg/ml; tetracycline, 10 μg/ml; kanamycin, 20 μg/ml; and for *A. tumefaciens*: carbenicillin, 100 μg/ml; tetracycline, 5 μg/ml; kanamycin, 100 μg/ml; rifampicin, 10 μg/ml; gentamycin, 100 μg/ml.

1.3b Construction of recombinant DNA plasmids and M13 phage

BamHI fragment 2 (FIG. 1) was cloned from the *Agrobacterium tumefaciens* plasmid pTiB$_6$806 (grown in strain A277) into pBR322 using standard procedures well known to those of ordinary skill in the art. Subfragments of BamHI fragment 2 were cloned into pBR325, pMK2004, or pUC13 (F. Bolivar et al. (1977) Gene 2:95–113, M. Kahn et al. (1979) Meth. Enzymol. 68:268–280, and J. Messing (1983) Meth. Enzymol. 101:20–78, respectively). All restriction endonuclease reactions were performed as suggested by the suppliers (Bethesda Research Laboratories (BRL), P. L. Biochemicals, or New England Biolabs). T4 DNA ligase was purchased from BRL. Recombinant plasmids were isolated from *E. coli* using a cleared lysate procedure (D. G. Blair et al. (1972) Proc. Natl. Acad. Sci. USA 69:2518–2522) or an alkaline lysis procedure (N. C. Birnboim and J. Doly (1979) Nucleic. Acids Res. 7:1513–1523).

Regions of BamHI fragment 2 to be used in $S_1$ nuclease protection reactions were cloned in both orientations into the replicative form DNA of M13mp8 and M13mp9 (obtained from Dr. N. Jones), or M13mp10 and M13mp11 (supplied by P. L. Biochemicals) by techniques well known to those of ordinary skill in the art.

1.3c RNA isolation, electrophoresis, blotting, and hybridization

Tumor RNA was isolated as previously described (S. B. Gelvin et al. (1981) Plasmid 6:17–29) except that after phenol extraction, polysaccharides were precipitated by the addition of one half volume cold 100% ethanol and incubation on ice for 15 min. After centrifugation at 10,000×g for 10 min, two volumes of 100% ethanol were added to the supernatant solution to precipitate the RNA.

Agarose gel electrophoresis through denaturing formaldehyde gels, blotting onto nitrocellulose, and hybridization were as described (Gelvin et al. (1981) supra) with the following modifications: The gels contained 2% agarose, and the wash solutions contained 1×SSC (0.15 M NaCl, 0.015M NaCitrate), 0.1% SDS, and 10 mM $Na_2$·EDTA. Nick translations were performed using Amersham nick translation kits.

1.3d Nuclease protection analysis of E9 tumor RNA

Hybridizations between recombinant M13 single-stranded DNA and E9 suspension RNA were performed in 20–30 μl of 5×SSC, 20 mM Tris-HCl (pH 7.4) at 65° C. Typically, 500 ng of recombinant phage DNA were hybridized with 20 μg of total RNA isolated from E9 suspension cultures. After 5 hr, the volume was brought to 150 μl with cold $S_1$ nuclease digestion buffer (280 mM NaCl, 50 mM NaOAc, 4.5 mM $ZnSO_4$, 20 μg/ml denatured calf thymus DNA, pH 4.6) and 100 units of $S_1$ nuclease (Sigma) were added. The samples were incubated at 37° C. for 45 min. Fifty μl of cold $S_1$ termination mix (2.5M NaOAc, 50 mM $Na_2$·EDTA) were added and the protected fragments precipitated by the addition of 20 μg yeast tRNA and 2.5 vol. of 100% ethanol.

After incubation at −20° C., the precipitates were collected, dissolved in 20 μl of alkaline buffer (30 mM NaOH, 2 mM $Na_2$·EDTA), and the fragments subjected to electrophoresis on 1.2% or 2.0% alkaline agarose gels (M. W. McDonnell et al. (1977) J. Mol. Biol. 110:119–146). Transfer of DNA to nitrocellulose, hybridization and washing of blots were as previously described (M. F. Thomashow et al. (1980) supra) except that the probe concentrations were generally less than 50 ng/ml and blots were routinely washed only in 0.3×SSC for 5 hr.

EXAMPLE 2

This Example teaches the construction of 1450bTxPR promoter vehicles suitable for homogenotization into $T_R$ of octopine-type Ti plasmids such as pTiA6 and pTi15955.

2.1 Cloning $T_R$

A recombinant DNA clone of the pTiA6 T-DNA BamHI fragment 2 in the BamHI site of pBR322 was digested to completion with EcoRI. (pTiA6 DNA, which is highly homologous to pTi15955 isolated from ATCC 15955, may be isolated from Agrobacterium tumefaciens A6NC). The digestion mixture containing a 5.4 kilobase pair (kbp) DNA fragment, EcoRI 13, was mixed with and ligated to EcoRI-linearized pRK290 DNA (G. Ditta et al. (1980) Proc. Natl. Acad. Sci. USA 77:7347–7357) and the mixture was transformed into E. coli K12 RR1. Plasmid DNA was isolated from tetracycline resistant transformants and a colony harboring a plasmid designated pRK290Eco13, containing the EcoRI 13 T-DNA fragment was identified by restriction enzyme analysis.

Figure 3:
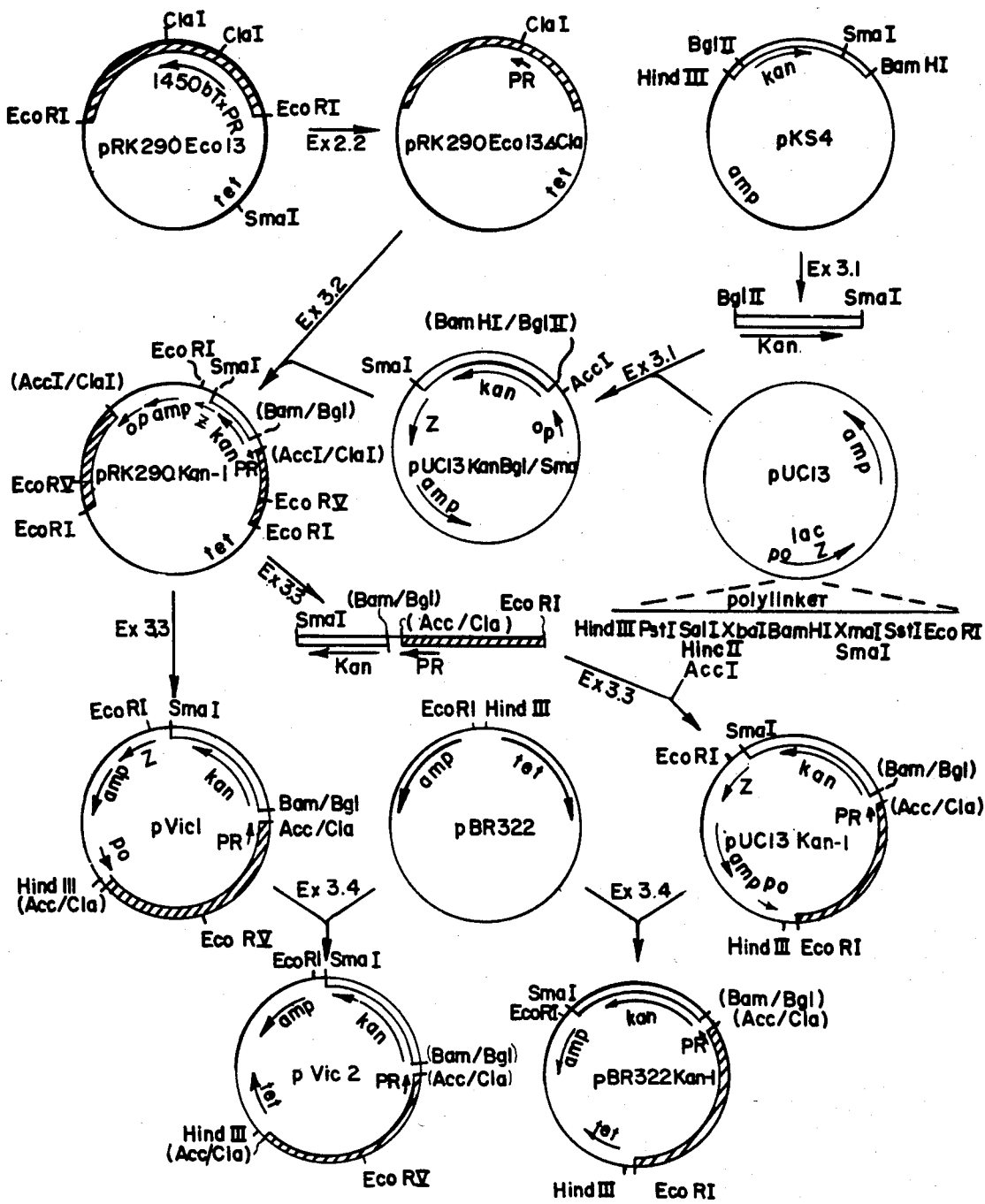
FIG. 3. is a schematic diagram, not drawn to scale, of DNA manipulations utilized in the Examples 2.2 through 3.4. Sites susceptable to the action of a restriction enzyme are indicated by that enzyme's name. A site that is no longer susceptable to the enzyme is indicated by the presence of parenthesis around the name of the enzyme. The extent and polarity of a promoter or a structural gene is indicated by arrows. Names of plasmids are within the circular representations of the plasmids. "Ex" refers to the Example which describes a particular manipulation. These conventions are also used in FIG. 5.

2.2 Deletion of the 1450bTx structural gene pRK290Eco13 DNA was digested to completion with ClaI, religated, and transformed into RR1. Plasmid DNA isolated from tetracycline resistant transformants was characterized by restriction analysis and a colony harboring a plasmid, designated pRK290Eco13ΔCla was identified, which was deleted for the ClaI fragment covering fragments $b_5$, c, and $d_1$ of FIG. 2. A foreign structural gene may be easily inserted behind the 1450bTx promoter region at the unique ClaI site of pRK290Eco13ΔCla (FIG. 3). The deletion of the ClaI fragment removed the first polyadenylation site 3' from the 1450bTx; however, two other polyadenylation site sequences are retained downstream from the remaining unique ClaI site.

2.3 Substitution of other restriction sites for the ClaI site

The following describes substitution of a HindIII site for the unique ClaI site of pRK290Eco13ΔCla. pRK290Eco13ΔCla DNA is isolated and digested to completion with ClaI. The resulting ClaI sticky-ends are filled in by incubation with the Klenow fragment of E. coli DNA polymerase I, and a double-stranded linker having the structure

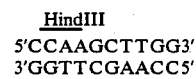

is blunt-end ligated into the now blunt-ended ClaI site. The resultant mixture is digested to completion with HindIII, religated, and transformed into RR1. Plasmid DNA isolated from tetracycline resistant transformants is screened by restriction analysis for lack of a ClaI site and the presence of a HindIII site at the location of the deleted 1450bTx structural gene, and such a plasmid is designated pRK290Eco13ΔClaHind.

Substitution of other linkers for that taught above can be used to change the ClaI site to the desired specificity of restriction enzymes other than HindIII, as will be evident to those of ordinary skill in the art. For example, BamHI linkers (obtainable from BRL) having the structure

were substituted for the HindIII linkers into a protocol that was otherwise essentially the same as that described above. An RR1 strain was identified which harbored a plasmid, designated herein as pRK290Eco13ΔClaBam, having a BamHI site at the location of the deleted 1450bTx structural gene.

EXAMPLE 3

This Example teaches the construction, diagrammed in FIG. 3, of selectable markers which confer resistance in both plants and bacteria to the antibiotic kanamycin and its analogs, e.g. neomycin and G418.

3.1 Preparation of the kan gene

A kanamycin resistance (kan) gene encoding the enzyme neomycin phosphotransferase II, the DNA sequence of which was reported by E. Beck et al. (1982) Gene 19:327–336, derived from the bacterial transposon Tn5 is present on the plasmid pKS4, which may be isolated from E. coli (pKS4) NRRL B-15394. pKS4 DNA was digested to completion with BglII and SmaI and a resultant 1 kbp NPTII-bearing fragment was mixed with and ligated to pUC13 which had been digested with SmaI and BamHI. BamHI and BglII sticky-ends have the same specificity (5'GATC . . . 3') and are easily ligatable together although the resulting BamHI/BglII suture,

is not susceptable to the action of either enzyme. The ligation mixture was transformed into E. coli K-12 JM83 (J. Messing (1979) Recomb. DNA Tech. Bull. 2(2):43–48, NIH Publ. No. 79–99) and transformants which produced white colonies were selected. Plasmid DNA was isolated from the selected transformants and characterized by restriction site mapping. A colony containing a plasmid, designated pUC13KanBgl/Sma, was identified.

The kan gene-bearing fragment of pUC13KanBgl/Sma has an AccI site in the pUC13 polylinker (a polylinker is a short sequence containing sites susceptable to a number of restriction enzymes) just upstream, relative to the kan structural gene, from the BamHI/BglII suture. The kan gene may be removed from pUC13KanBgl/Sma by digestion with SmaI and AccI on a 1 kbp DNA fragment. This particular AccI cut has sticky-ends, 5'CG . . . 3', which are easily ligatable to those produced by the enzyme ClaI.

3.2 Insertion of kan behind the 1450bTxPR promoter pUC13KanBgl/Sma and pRK290Eco13ΔCla were linearized by digestion to completion with AccI and ClaI, respectively, mixed with and ligated to each other, and transformed into E. coli RR1. Plasmid DNAs isolated from transformants resistant to ampicillin and tetracycline (respectively selecting for pUC13 and pRK290 sequences) are characterized by restriction enzyme analysis. A colony was identified which contained a plasmid, designated pRK290Kan-1, which had the kan gene inserted behind the 1450bTx promoter in the same orientation and position formerly occupied by the 1450bTx coding sequence. When the kan gene of pRK290Kan-1 is being transcribed, RNA polymerase II must transcribe all of the Tn5 and all of the pUC13 sequences before reaching the first T-DNA polyadenylation site 3' to the kan gene. However, there are other sequences 3' to the kan/pUC13 suture which may serve as polyadenylation sites.

Figure 4:
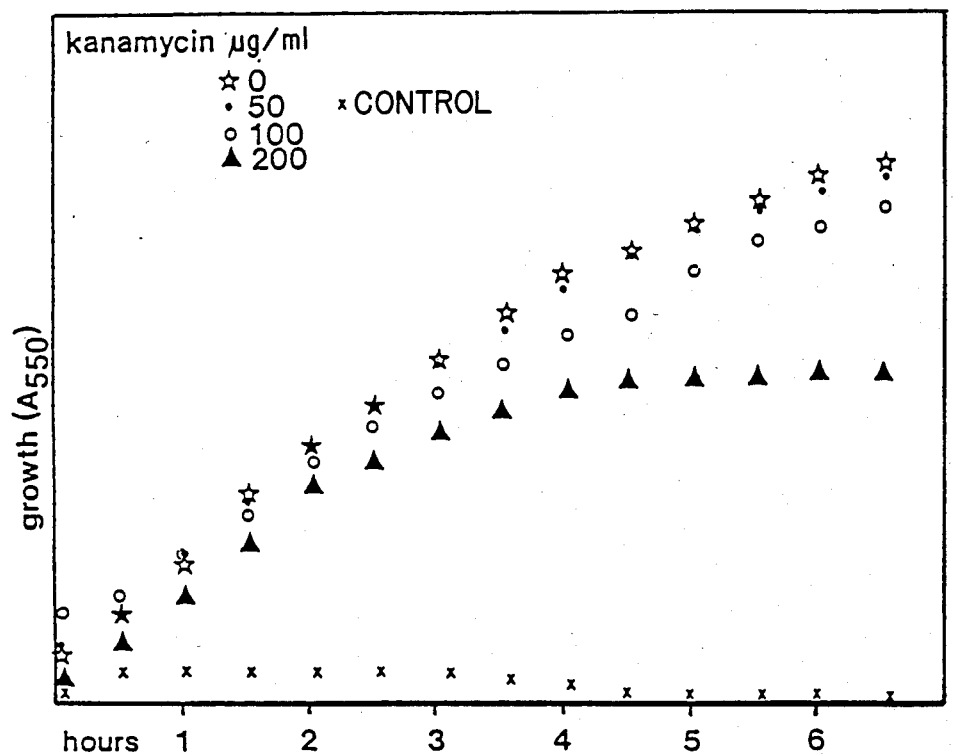
FIG. 4. disclosed the changed growth characteristics of bacterial cells containing a 1450bTx promoter region/NPTII structural gene combination, indicating that the promoter region is active in *A. tumefaciens* and that the combination confers resistance to kanamycin.

3.3 Deletion of pRK290 from pRK290Kan-1 pRK290-based plasmids are fairly large (more than 20 kbp) and are therefore often difficult to handle while doing recombinant DNA manipulations. The construction of two plasmids which replicate via the pUC13 replicon is described below and diagrammed schematically in FIG. 3.

pRK290Kan-1 DNA was digested to completion with EcoRV, ligated to itself, and transformed into JM83. Plasmids were isolated from ampicillin resistant tetracycline sensitive transformants and were characterized by restriction analysis and a colony was identified which contained a plasmid designated pVic1, having sequences for pUC13, kan, and the EcoRV T-DNA fragment, deleted for the 1450bTx structural gene, which carried the 1450bTx promoter (part of fragment $d_2$, as in FIG. 2) and two 1450bTx-associated polyadenylation sites ($b_4$ and part of $b_3$). pVic1, being homologous to T-DNA on both sides of the 1450bTx structural gene, is suitable for integration into octopine-type Ti plasmids by double homologous recombination after direct transformation of A. tumefaciens cells and selection for carbenicillin resistance. After homogenotization, the T-DNA will not have a functional 1450bTx gene and will not cause transformed plant cells to make the opines mannopine or agropine. After cointegration, the construction confirs carbenicillin resistance to bacteria and in plant cells allows agropine and mannopine synthesis.

pRK290Kan-1 DNA was digested with SstI, EcoRI, and HindIII. pUC13 DNA was digested with SstI and EcoRI. After the digested pRK290Kan-1 and pUC13 DNAs were mixed with and ligated to each other, the ligaton mix was transformed into JM83. Plasmid DNAs were isolated from white, ampicillin resistant colonies and characterized by restriction enzyme analysis and a colony was identified which contained a plasmid, designated pUC13Kan-1, having sequences for pUC13, kan, and T-DNA fragment $d_2$ (as in FIG. 2), which carries the 1450bTxPR. pUC13Kan-1, being homologous to T-DNA on one side of the 1450bTx structural gene is suitable for integration into octopine-type Ti plasmids by single homologous recombination after direct transformation of *A. tumefaciens* cells and selection for carbenicillin resistance. After cointegration, the T-DNA will contain a duplication of fragment $d_2$, must be maintained under carbenicillin selection, will retain a functional 1450bTx gene, and will allow transformed plant cells to make the opines mannopine and/or agropine.

3.4 Construction of a mobilizable vector

The pUC series of plasmids (e.g. pUC13-based plasmids) cannot be mobilized for conjugal transfer from *E. coli* to *A. tumefaciens* by pRK2013 and must therefore be directly transformed into the recipient Agrobacterium cells. However, as pBR322-based plasmids can be mobilized by pRK2013 but do not replicate in Agrobacterium, such a plasmid is a useful suicide vector for the transfer of the 1450bTxPR/kan selectable marker into octopine-type Ti plasmids.

pVic1 and pBR322 DNA, each digested by HindIII and EcoRI, were mixed, ligated together, and transformed into RR1. Plasmid DNAs isolated from ampicillin resistant transformants were characterized by restriction mapping and a colony was identified which harbored a plasmid, designated pVic2, having a copy of pBR322 substituted for the pUC13 sequences of pVic1. pVic2 is a mobilizable suicide vector capable of cointegration or homogenotization into $T_R$.

pUC13Kan-1 DNA and pBR322 DNA, each digested by HindIII and EcoRI are mixed, ligated together, and transformed into RR1. Plasmid DNAs isolated from ampicillin resistant transformants are characterized by restriction mapping and a colony is identified which harbored a plasmid, designated pBR322Kan-1, having a copy of pBR322 substituted for the pUC13 sequences of pUC13Kan-1. pBR322Kan-1 is a mobilizable suicide vector capable of cointegration into $T_R$.

EXAMPLE 4

This Example discloses the unexpected result that, when placed behind the 1450bTx promoter region, the bacterial structural gene for kanamycin resistance was expressed in both eukaryotic cells, specifically plant cells, and in prokaryotic cells, specifically Agrobacterium and *E. coli* cells, thereby demonstrating the previously undisclosed fact that the 1450bTxPR may be used as part of a dual-purpose promoter region/foreign structural gene combination.

4.1 Kanamycin resistance in prokaryotes

*A. tumefaciens* A348, previously known in the art, was derived by introduction of an octopine-type plasmid, pTiA6, into a rifampicin resistant derivative, A136, of a heat-cured avirulent derivative, A114(NTI) of the nopaline-type strain C58. pRK290Kan-1 was introduced into A348 by transformation but was not homogenotized into pTiA6 at that time. The resulting strain, A348-pRK290-Kan1, was observed to grow when plated on media containing 100 μg/ml kanamycin. Growth curves of this strain in liquid culture (YEP broth at 30° C.) showed generally equivalent growth rates at all kanamycin concentrations tested, although at the highest concentration, 200 μg/ml, the curve plateaued sooner than was observed at lower drug concentrations (FIG. 4).

4.2 Kanamycin resistance in eukaryotes

A348-pRK290Kan-1 was homogenotized into pTiA6 and used to transform plant cells. The upward-facing ends of inverted sunflower hypocotyl sections (see K. A. Barton et al. (1983) Cell 32:1033–1043) were inoculated and after 2–4 weeks the resulting calli were placed on solidified MS3 media lacking hormones (Example 1.3a). Agrobacterium cells were killed with 1 mg/ml carbenicillin and 200 μg/ml vancomycin and the calli were grown until they were approximately 2.5 cm in diameter. Small pieces of callus were transferred to solidified MS3 media lacking hormones and supplemented with carbenicillin, vancomycin, and 25 μg/ml G418, an analog of kanamycin. Many of the pieces remained green and continued to grow while other pieces, probably derived from untransformed cells contaminating the calli, died. All of the controls, which consisted of zein sequences in either orientation substituting for the kan structural gene were killed by the G418. This demonstrated that the plant cells transformed by the 1450bTxPR/kan structural gene combination can be resistant to the action of a kanamycin.

EXAMPLE 5

This Example teaches the unexpected result that eukaryotic structural genes placed behind the 1450bTx promoter region are expressed in both eukaryotic and prokaryotic cells.

Lectins are nutritionally important seed protens and are thought to be important during establishment of legume-Rhizobium symbioses. pPVL134, which may be obtained from *E. coli* HB101 (pPVL134), ATCC 39181, contains a cDNA structural gene for a lectin from the seeds of *Phaseolus vulgaris* L. (L. M. Hoffman et al. (1982) Nucl. Acids Res. 10:7819–7828). The coding sequences of the cDNA are identical to those of the gene itself as the gene is uninterrupted by introns.

5.1 Construction of expression vectors

*E. coli* HB101 methylates DNA so that the DNA is not cleavable by the enzyme BclI; however, *E. coli* GM33 and several other strains known in the art do not protect BclI sites by methylation. pPVL134 DNA, isolated from HB101 (pPVL134), is transformed into GM33 and tetracycline resistant transformants are identified. pPVL134 DNA isolated from GM33 (pPVL134) is linearized by digestion to completion with BclI, treated with BAP, mixed with and ligated to BamHI-digested pRK290Eco13ΔClaBam, and transformed into RR1. Plasmid DNAs isolated from tetracycline resistant transformants are characterized and a colony is selected which harbors a plasmid, designated pRK290Lec-1, having pPVL134 insert oriented so that the 1450bTxPR is immediately upstream from the lectin coding sequence. The orientation of the lectin gene may be determined by the presence of ClaI sites 0.09 kbp and 0.78 kbp from the 5'- and 3'-ends, respectively, of the insert. Both ends form uncleavable BamHI/BclI sutures after ligation into pRK290Eco13ΔClaBam.

pRK290Lec-1 DNA is transfered into A348 (pTiA6) by either transformation or matings followed by introduction of pPH1J1 to exclude independent pRK290 replicons and selection for tetracycline resistant cells. For expression of the lectin gene, homogenotes need not be isolated but, if desired, may be identified by screening the descendants of tetracycline resistant cointegrates by restriction enzyme analysis. TIP plasmids resulting from either cointegration or homogenotization events of pTiA6 with pRK290Lec-1 are designated herein as pTiA6Lec-1.

5.2 Expression in prokaryotes

RR1 (pRK290Lec-1) and A348 (pTiA6Lec-1) are screened by electrophoretic and hybridization methods and are observed to contain the appropriate plant RNA sequences.

5.3 Expression in eukaryotes

A348 (pTiA6Lec-1) is inoculated onto inverted sunflower stems and the resultant crown gall tumors are observed by hybridization, electrophoretic, and immunological methods, known to those of ordinary skill in the art, to contain lectin mRNA and protein sequences.

EXAMPLE 6

This Example teaches the construction of sub-Ti plasmids which include all of $T_R$. $T_R$ carries none of the genes which cause a phenotype in transformed cells of hormone-independent growth. Also note that when ocs is available to function as a selectable marker on some of the plasmids discussed herein, the need to use the 1450bTxPR to promote expression of a selectable marker (e.g. kan) is eliminated.

Figure 5:
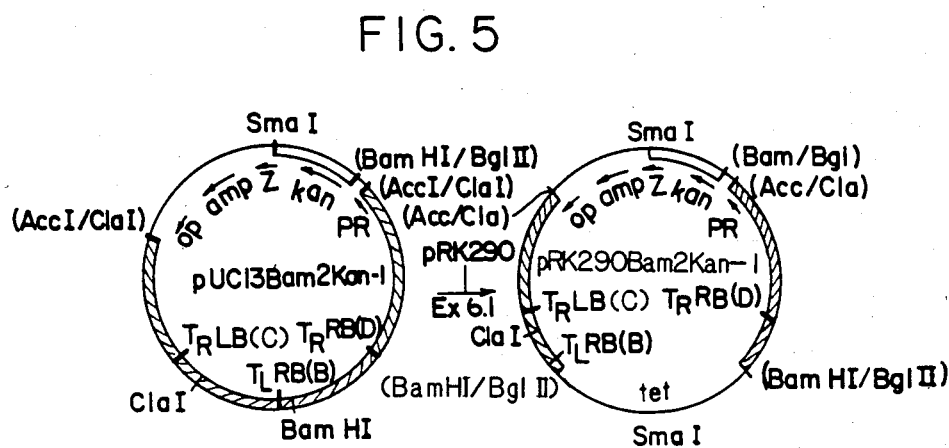
FIG. 5. is a schematic diagram, not drawn to scale, of DNA manipulations described in Example 6.1.

6.1 Construction of $T_R$ sub-Ti plasmids pRK290Kan-1 was transferred into A348 (pTiA6) by means of transformation. After homogenotization, which deletes the 1450bTx structural gene and results in an opine synthesis phenotype, Ti plasmid DNAs isolated from kanamycin resistant Agrobacterium cells are characterized by restriction analysis. A DNA sample that is the result of a homogenotization event rather than a cointegration event is digested with BamHI and ligated to itself. The resulting mixture is transformed into JM83. Plasmid DNA from transformants resistant to kanamycin and/or ampicillin are characterized by restriction analysis and a colony is identified which harbors a nonmobilizable, *E. coli* maintainable plasmid, designated pUC13Bam2Kan-1 (FIG. 5).

pUC13Bam2Kan-1 and pRK290 DNAs are respectively digested with BamHI and BglII and are then mixed with and ligated to each other. The ligated mixture is digested with BamHI and BglII to linearized nonhybrid molecules, and transformed into RR1. (pBR322Bam2Kan-1 may be substituted for pUC13Bam2Kan-1, if the plasmid is linearized by partial digestion with BamHI.) Plasmid DNAs isolated from transformants resistant to ampicillin and/or kanamycin and tetracycline are characterized by restriction analysis. A colony is identified which harbors a plasmid, designated pRK290Bam2Kan-1 (FIG. 5), having single copies each of the two parental plasmids, sutured together in either orientation at two hybrid BglII/BamHI sites. pRK290Bam2Kan-1 is transferred to a vir gene-containing Agrobacterium strain by a triparental mating between the Agrobacterium (vir) strain, E. coli RR1 (pRK290Bam2Kan-1), and E. coli (pRK2013). In variance with the normal triparental mating procedure, pPH1J1 is not then introduced as it is incompatible with pRK290 replicons, pRK290Bam2Kan-1 being designed for independent replication within the Agrobacterium (vir) strain.

6.2 Variant $T_R$ sub-Ti plasmids

The vector described in Example 6.1 is based on BamHI fragment 2 and therefore includes the $T_L$ right border ($T_LRB(B)$) in addition to both borders of $T_R$ ($T_RLB(C)$) and $T_RRB(D)$). Other enzymes, which do not cleave $T_R$ of the octopine-type plasmid pTi15955 and which may prove useful in construction of sub-Ti plasmids, include ApaI and SmaI (ocs. part of tml), MluI and HpaI (part of ocs), and KpnI (ocs, tml, ORF9). (The $T_L$ structural genes or open reading frames (ORFs) listed parenthetically are included on the fragment generated by the preceeding enzyme.) Other enzymes, e.g. HindIII (ocs, tml. ORF9, tmr, part of ORF5/tms) and BglI (ocs), which normally cut $T_R$ DNA do not cut $T_R$ derivatives which are deleted from the ClaI fragment covering fragments b5, c, and d1 of FIG. 2. Those skilled in the art will note that the kan sequence contains a BglI site and that there are HindIII sites in pBR322 and the pUC-series plasmids. Judicious use of partial BglI or HindIII digestion conditions, well understood in the art, will be needed when constructing sub-Ti plasmids based on the selectable marker constructions described herein.

Other enzymes such as AatII and ClaI may be utilized for construction of pTi15955-based $T_R$ sub-Ti plasmids which do not include $T_LRB(B)$. In particular, when grown in an appropriate methylating host, e.g. E. coli K802 (W. B. Wood (1966) J. Mol. Biol. 16:118), homogenotized T-DNA derivatives of pRK290Kan-1, pVic1, and pVic2 have no unmethylated cleavable ClaI site within $T_R$, but do have a cleavable ClaI site between $T_RLB(C)$ and $T_LRB(B)$ (see FIG. 5). pUC1-3Bam2Kan-1 or pBR322Bam2Kan-1 DNA grown in K802 is digested with BamHI and ClaI. The DNA is ligated together by use of appropriate linkers or by blunting of sticky-ends with the Klenow fragment of E. coli DNA polymerase I, resulting in the deletion of $T_LRB(B)$. Digestion under controlled conditions of BamHI-linearized pUC13Bam2Kan-1 with the nuclease Bal31 can also be used to remove $T_LRB(B)$.

6.3 Mini-Ti plasmids

Mini-Ti plasmids may similarly be constructed by use of the enzymes EcoK, which does not cleave pTi15955 T-DNA, and MstII, which has a single pTi15955 T-DNA cleavage site that is removed by deletion of the ClaI fragment covering fragments b5, c, and d1. The MstI sticky-ends must be blunted before ligation with the Klenow fragment of DNA polymerase I, and the EcoK ends must be blunted by actions of both the Klenow fragment and T4 DNA polymerase.

In order to reduce the size of the sub-Ti plasmids discussed herein, smaller vectors may be substituted for pRK290. Plasmids other than those referenced in Background Shuttle Vectors that can be maintained in Agrobacterium include, but are not limited to, those described by R. C. Tait et al. (1982) Gene 20:39-49, J. Leemans et al. (1982) Gene 19:361-364, and J. Hille and R. Schilperoort (1981) Plasmid 6:360-362.

EXAMPLE 7

Triparental matings were generally accommplished as described below; other variations known to those skilled in the art are also acceptable. E. coli RR1 (pRK290-based shuttle vector) or E. coli K802 (pRK290-based shuttle vector) was mated with E. coli RR1 (pRK2013) and A348, a TIP plasmid harboring A. tumefaciens strain resistant to rifampicin. The pRK2013 was transferred to the shuttle vector carrying strain and mobilized the shuttle vector for transfer to the Agrobacterium. Growth on a minimal medium incapable of supporting the growth of E. coli, AB glucose, containing both rifampicin and the drug to which the shuttle vector is resistant, often either kanamycin or carbenicillin (an ampicillin analog), resulted in the selection of Agrobacterium cells containing shuttle vector sequences. A mating of these cells with E. coli (pPH1J1), strain 2104, resulted in the transfer of pPH1J1 to the Agrobacterium cells. pPH1J1 and pRK290-based shuttle vectors cannot coexist for long in the same cell. Growth on gentamycin and kanamycin select for cells which have Ti plasmids that have undergone single- or double-homologous recombination events (cointegration or homogenotization, respectively) with the shuttle vector and now carry the desired construction. The concentrations of antibiotics used for selection were as described in Example 1.3a. E. coli strains were usually grown at 37° C. in L-broth supplemented with 0.2% casamino acids, and A. tumefaciens strains at 30° C. in YEP medium. pRK290 and pRK2013 were disclosed by G. Ditta et al. (1980) Proc. Natl. Acad. Sci. USA 77:7347-7357, and pPH1J1 by P. R. Hirsh (1978) Thesis, Univ. E. Anglia.

I claim:

1. In a method of genetically modifying a cell comprising the steps of:
   (a) transforming a prokaryotic cell with a DNA molecule comprising a promoter region 5' from a foreign structural gene, wherein said promoter region causes transcription of said structural gene in prokaryotes, and
   (b) detecting expression of said gene in a resultant prokaryotic strain,
the improvement comprising transforming said prokaryotic cell with a DNA molecule comprising a T-DNA gene promoter region 5' from a foreign structural gene, said foreign structural gene not being under control of said promoter in nature, and said T-DNA region being capable of causing transcription of said gene in plant cells as well as prokaryotes.

2. In a method for transforming transformable plant cell with a DNA molecule comprising a promoter region 5' from a foreign structural gene, wherein said promoter region causes transcription of said structural gene in plant cells by:
   (a) transforming a transformable plant cell with said DNA molecule; and
   (b) detecting expression of said gene in a resultant plant tissue, the improvement comprising utilizing the method of claim 1 to first transform a prokaryotic cell with said DNA molecule and detect expression of said gene therein.

3. A method according to claim 2 wherein said promoter region is hybridizable under conditions of appropriate stringency to the 1450Tx gene promoter.

4. A method according to claim 2 wherein said promoter region is the T-DNA 1450bTx gene promoter.

5. A method according to claim 2 wherein said structural gene encodes a resistance to an antibiotic selected from the group consisting of kanamycin, neomycin, G418 and an analog thereof.

6. A method according to claim 5 wherein said structural gene encodes neomycin phosphotransferase II from Tn5.

7. A method according to claim 2 wherein said DNA molecule is linked to a replicon that cannot be maintained independently in a bacterium of the family Rhizobiaceae.

8. A method according to claim 2 wherein said DNA molecule is linked to a replicon that can be maintained independently in a bacterium of the family Rhizobaceae.

9. A method according to claim 2 wherein said DNA molecule is linked to one or more of the repetitive sequences selected from the group consisting of $T_LLB(A)$, $T_LRB(B)$, $T_RLB(C)$ and $T_RRB(D)$.

10. A method according to claim 2 wherein said structural gene is ligated to the left end of the DNA fragment $d_2$ of the TR section of T-DNA.

11. A method according to claim 10 wherein said structural gene is ligated to the right end of the T-DNA fragment $b_4$ of the TR section of T-DNA.

12. A DNA vector comprising
(a) a T-DNA region containing structural elements essential for transfer of said T-DNA region into a dicot plant genome; and
(b) one or more T-DNA promoter regions 5' from a foreign structural gene inserted in said T-DNA region and capable of conferring an identifiable phenotype, said promoter region being a T-DNA gene promoter region that causes transcription both in prokaryotes and in dicot plant cells, said foreign structural gene being a gene which is not under the control of said promoter in nature, said promoter region and foreign strucutral gene being inserted in said T-DNA region so that the transfer activity of the T-DNA is not disrupted, and said foreign structural gene being the sole means for said vector to confer said identifiable phenotype to a bacterial strain transformed by said vector.

13. A vector according to claim 12 wherein said promoter region is hybridizable under conditions of appropriate stringency to the 1450bTx gene promoter.

14. A vector according to claim 12 wherein said promoter region is the T-DNA 1450bTx gene promoter.

15. A vector according to claim 12 wherein said structural gene confers an identifiable phenotype in a plant cell transformed to contain said structural gene.

16. A vector according to claim 15 wherein said identifiable phenotype is a resistance to an antibiotic selected from the group consisting of kanamycin, neomycin, G418 and an analog thereof.

17. A vector according to claim 16 wherein said structural gene encodes neomycin phosphotransferase II from Tn5.

18. A vector according to claim 17 wherein said vector is selected from the group consisting of pRK290K and-1 and functionally equivalent pRK290 based shuttle vectors.

19. A bacterial strain comprising the vector of claim 18.

20. A vector according to claim 12, further comprising a replicon that cannot be maintained independently in a bacterium of the family Rhizobiaceae.

21. A vector according to claim 12, further comprising a replicon that can be maintained independently in a bacterium of the family Rhizobiaceae.

22. A vector according to claim 12, further comprising one or more of the repetitive sequences selected from the group consisting of $T_LLB(A)$, $T_LRB(B)$. $T_RLB(C)$ and $T_RRB(D)$.

23. A vector according to claim 12 wherein said structural gene is ligated to the left end of the DNA fragment $d_2$ of the TR section of T-DNA.

24. A vector according to claim 23 wherein said structural gene is ligated to the right end of the DNA fragment $b_4$ of the TR section of T-DNA.

* * * * *

UNITED STATES PATENT AND TRADEMARK OFFICE
CERTIFICATE OF CORRECTION

PATENT NO. : 4,771,002
DATED : Sep. 13, 1988
INVENTOR(S) : Stanton B. Gelvin

It is certified that error appears in the above-identified patent and that said Letters Patent is hereby corrected as shown below:

On the first page of the patent after "[73] Assignee: Lubrizol Genetics, Inc., Wickliffe, Ohio" please add --and Purdue Research Foundation, West Lafayette, Indiana--.

IN THE CLAIMS

At claim 2, line 1, please insert --a-- after "transforming".

At claim 3, line 3, please delete "1450Tx" and insert --1450bTx--.

At claim 8, line 3, please delete "Rhizoba-" and insert --Rhizobia- --.

At claim 18, line 2, please delete "pRK290K" and insert --pRK290Kan--.

At claim 18, line 3, please delete the "and" before "-1".

Signed and Sealed this

Seventeenth Day of October, 1989

Attest:

DONALD J. QUIGG

Attesting Officer

Commissioner of Patents and Trademarks